United States Patent
Velez et al.

(10) Patent No.: US 11,448,632 B2
(45) Date of Patent: Sep. 20, 2022

(54) SYSTEM AND METHOD FOR THE DETERMINATION OF PRODUCE SHELF LIFE

(71) Applicant: Walmart Apollo, LLC, Bentonville, AR (US)

(72) Inventors: Ckristian Velez, Bentonville, AR (US); Mohit Mehrotra, Kadubeesanahalli (IN)

(73) Assignee: Walmart Apollo, LLC, Bentonville, AR (US)

(*) Notice: Subject to any disclaimer, the term of this patent is extended or adjusted under 35 U.S.C. 154(b) by 0 days.

(21) Appl. No.: 16/036,456

(22) Filed: Jul. 16, 2018

(65) Prior Publication Data
US 2019/0285603 A1    Sep. 19, 2019

(30) Foreign Application Priority Data
Mar. 19, 2018 (IN) .............................. 201811009903

(51) Int. Cl.
| | | |
|---|---|---|
| G01N 33/02 | (2006.01) | |
| G06Q 10/04 | (2012.01) | |
| G06Q 10/08 | (2012.01) | |

(52) U.S. Cl.
CPC .......... *G01N 33/025* (2013.01); *G06Q 10/04* (2013.01); *G06Q 10/087* (2013.01)

(58) Field of Classification Search
CPC .............................. G01N 33/025; G06Q 10/04
See application file for complete search history.

(56) References Cited

U.S. PATENT DOCUMENTS

| | | |
|---|---|---|
| 4,750,197 A | 6/1988 | Denekamp |
| 5,369,995 A | 12/1994 | Scheinbeim |
| (Continued) | | |

FOREIGN PATENT DOCUMENTS

| | | |
|---|---|---|
| CA | 2469699 | 1/2016 |
| CN | 1789992 | 6/2006 |
| (Continued) | | |

OTHER PUBLICATIONS

Anzilotti, Eillie; "These High-Tech Sensors Track Exactly How Fresh Our Produce Is So We Stop Wasting Food"; https://www.fastcompany.com/40424163/these-high-tech-sensors-track-exactly-how-fresh-our-produce-is-so-we-stop-wasting-food; May 26, 2017; pp. 1-3.

(Continued)

*Primary Examiner* — A. Hunter Wilder
(74) *Attorney, Agent, or Firm* — Fitch, Even, Tabin & Flannery, LLP

(57) ABSTRACT

A system and a method for the determination of product shelf life in a supply chain environment are discussed. The system receives periodic readings from various sensors that are associated with a shipment of produce. The system determines ambient deviations throughout the supply chain for temperature, humidity and ethylene. The system determines a product shelf life based on a calculated sensitivity and exposure to temperature, humidity, and ethylene. The system determines a remaining shelf life based on the determined product shelf life, and generates an event based on the remaining shelf life meeting a threshold. The system updates an indication of the remaining shelf life on a graphical interface for action.

13 Claims, 4 Drawing Sheets

(56) References Cited

U.S. PATENT DOCUMENTS

| | | |
|---|---|---|
| 5,621,162 A | 4/1997 | Yun |
| 5,671,362 A | 9/1997 | Cowe |
| 5,774,053 A | 6/1998 | Porter |
| 5,791,497 A | 8/1998 | Campbell |
| 5,835,012 A | 11/1998 | Wilk |
| 6,204,763 B1 | 3/2001 | Sone |
| 6,285,282 B1 | 9/2001 | Dorenbosch et al. |
| 6,294,997 B1 | 9/2001 | Paratore et al. |
| 6,296,187 B1 | 10/2001 | Shearer |
| 6,386,454 B2 | 5/2002 | Hecht |
| 6,435,002 B1 | 8/2002 | Briggs |
| 6,497,367 B2 | 12/2002 | Conzola |
| 6,549,135 B2 | 4/2003 | Singh et al. |
| 6,600,418 B2 | 7/2003 | Francis |
| 6,624,752 B2 | 9/2003 | Klitsgaard |
| 6,779,722 B1 | 8/2004 | Mason |
| 6,847,447 B2 | 1/2005 | Ozanich |
| 6,865,516 B1 | 3/2005 | Richardson |
| 6,876,990 B2 | 4/2005 | Yamanishi |
| 6,965,871 B1 | 11/2005 | Szabo |
| 6,970,100 B2 | 11/2005 | Lovegreen |
| 6,982,640 B2 | 1/2006 | Lindsay |
| 7,004,621 B2 | 2/2006 | Roberts |
| 7,027,958 B2 | 4/2006 | Singh |
| 7,057,495 B2 | 6/2006 | Debord |
| 7,065,501 B1 | 6/2006 | Brown |
| 7,148,803 B2 | 12/2006 | Bandy |
| 7,185,810 B2 | 3/2007 | White |
| 7,245,386 B2 | 7/2007 | Philipps |
| 7,248,147 B2 | 7/2007 | Debord |
| 7,271,720 B2 | 9/2007 | Tabe |
| 7,271,724 B2 | 9/2007 | Goyal |
| 7,287,694 B2 | 10/2007 | Banavar |
| 7,298,257 B2 | 11/2007 | Suzuki |
| 7,347,361 B2 | 3/2008 | Lovett |
| 7,372,003 B2 | 5/2008 | Kates |
| 7,434,724 B2 | 10/2008 | Lane |
| 7,455,225 B1 | 11/2008 | Hadfield |
| 7,487,913 B2 | 2/2009 | Adema |
| 7,495,558 B2 | 2/2009 | Pope et al. |
| 7,543,741 B2 | 6/2009 | Lovett |
| 7,560,013 B2 | 7/2009 | Shekarriz |
| 7,673,464 B2 | 3/2010 | Bodin |
| 7,675,424 B2 | 3/2010 | Debord |
| 7,693,739 B2 | 4/2010 | Schmidtberg |
| 7,757,947 B2 | 7/2010 | Reznik |
| 7,769,221 B1 | 8/2010 | Shakes |
| 7,775,130 B2 | 8/2010 | Harish |
| 7,792,711 B2 | 9/2010 | Swafford, Jr. |
| 7,796,038 B2 | 9/2010 | Batra |
| 7,810,720 B2 | 10/2010 | Lovett |
| 7,835,885 B2 | 11/2010 | Ben-Tzur |
| 7,937,244 B2 | 5/2011 | Kadaba |
| 7,954,712 B2 | 6/2011 | Babcock |
| 7,960,176 B2 | 6/2011 | Louvet |
| 7,967,201 B2 | 6/2011 | Bowlus |
| 7,978,060 B2 | 7/2011 | Mandava |
| 8,072,605 B2 | 12/2011 | Costa |
| 8,102,101 B2 | 1/2012 | Giurgiutiu |
| 8,112,303 B2 | 2/2012 | Eglen |
| 8,203,603 B2 | 6/2012 | Harbert |
| 8,279,065 B2 | 10/2012 | Butler |
| 8,306,871 B2 | 11/2012 | Farmer |
| 8,325,036 B1 | 12/2012 | Fuhr |
| 8,334,970 B2 | 12/2012 | Wildenbeest |
| 8,354,927 B2 | 1/2013 | Breed |
| 8,412,590 B2 | 4/2013 | Elliott |
| 8,447,665 B1 | 5/2013 | Schoenharl |
| 8,626,193 B1 | 1/2014 | Crossno |
| 8,682,760 B2 | 3/2014 | Cameo |
| 8,786,407 B2 | 7/2014 | Liu |
| 8,803,970 B2 | 8/2014 | Weisensale |
| 8,870,453 B2 | 10/2014 | Branch |
| 8,947,234 B2 | 2/2015 | Doan |
| 8,989,053 B1 | 3/2015 | Skaaksrud |
| 8,994,508 B2 | 3/2015 | Dacus |
| 9,024,755 B2 | 5/2015 | Fuhr |
| 9,030,295 B2 | 5/2015 | Allen |
| 9,031,990 B2 | 5/2015 | Scott |
| 9,218,585 B2 | 12/2015 | Gupta et al. |
| 9,244,147 B1 | 1/2016 | Soundararajan |
| 9,275,361 B2 | 3/2016 | Meyer |
| 9,316,595 B2 | 4/2016 | Wakita |
| 9,350,734 B1 | 5/2016 | Jamshidi |
| 9,366,483 B2 | 6/2016 | Eckhoff |
| 9,443,217 B2 | 9/2016 | Iyer |
| 9,449,208 B2 | 9/2016 | Luk |
| 9,514,323 B2 | 12/2016 | Mehring |
| 9,524,648 B1 | 12/2016 | Gopalakrishnan |
| 9,557,224 B2 | 1/2017 | Eisenstadt et al. |
| 9,569,944 B2 | 2/2017 | Barnes |
| 9,710,754 B2 | 7/2017 | Kaye |
| 9,766,114 B2 | 9/2017 | Ademe |
| 9,789,518 B2 | 10/2017 | Iino |
| 9,794,165 B1 | 10/2017 | Wood |
| 9,811,632 B2 | 11/2017 | Grabiner |
| 9,824,298 B1 | 11/2017 | Krishnan Gorumkonda |
| 9,835,498 B2 | 12/2017 | Haarer |
| 9,888,214 B2 | 2/2018 | Bateman |
| 9,915,638 B2 | 3/2018 | Pakstaite |
| 10,009,667 B2 | 6/2018 | Taylor |
| 10,060,798 B1 | 8/2018 | Riscalla |
| 10,089,556 B1 | 10/2018 | Xu |
| 10,176,451 B2 | 1/2019 | Nemet |
| 10,187,593 B2 | 1/2019 | Holmes |
| 10,223,610 B1 | 3/2019 | Akselrod-Ballin |
| 10,281,200 B2 | 5/2019 | Johnston |
| 10,285,433 B2 | 5/2019 | Ademe |
| 10,324,439 B2 | 6/2019 | Lagares-Greenblatt |
| 10,373,472 B2 | 8/2019 | Johnston |
| 10,386,827 B2 | 8/2019 | Enver |
| 10,423,918 B2 | 9/2019 | Mehring |
| 10,445,684 B2 | 10/2019 | Mehring |
| 10,452,959 B1 | 10/2019 | Gautam |
| 10,466,111 B2 | 11/2019 | Jones |
| 10,546,162 B1 | 1/2020 | Diorio |
| 10,552,654 B2 | 2/2020 | Beckmann |
| 10,572,851 B2 | 2/2020 | Skaaksrud |
| 10,591,306 B2 | 3/2020 | High |
| 10,594,956 B2 | 3/2020 | Holmes |
| 10,676,794 B2 | 6/2020 | Amini |
| 10,956,856 B2 | 3/2021 | Ma |
| 11,070,895 B2 | 7/2021 | Taylor |
| 11,138,554 B2 | 10/2021 | Johnsen |
| 2001/0045449 A1 | 11/2001 | Shannon |
| 2002/0119513 A1 | 8/2002 | Alocilja |
| 2003/0088442 A1 | 5/2003 | Michael |
| 2003/0214387 A1 | 11/2003 | Giaccherini |
| 2004/0018641 A1 | 1/2004 | Goldsmith |
| 2004/0069046 A1 | 4/2004 | Sunshine |
| 2004/0074957 A1 | 4/2004 | Devar |
| 2004/0148117 A1 | 7/2004 | Kirshenbaum |
| 2004/0154739 A1 | 8/2004 | Shanahan |
| 2004/0204881 A1 | 10/2004 | Mayer |
| 2004/0226392 A1 | 11/2004 | McNally |
| 2004/0233055 A1 | 11/2004 | Canich |
| 2005/0060246 A1 | 3/2005 | Lastinger |
| 2005/0061877 A1 | 3/2005 | Stevens |
| 2005/0075954 A1 | 4/2005 | Matsumoto |
| 2005/0104730 A1 | 5/2005 | Yang |
| 2005/0149470 A1 | 7/2005 | Fujie |
| 2005/0197912 A1 | 9/2005 | Wittmer |
| 2005/0203790 A1 | 9/2005 | Cohen |
| 2005/0222889 A1 | 10/2005 | Lai |
| 2005/0228712 A1 | 10/2005 | Bornstein |
| 2006/0006987 A1 | 1/2006 | Hashimoto |
| 2006/0011721 A1 | 1/2006 | Olsen |
| 2006/0018274 A1 | 1/2006 | Twitchell |
| 2006/0071774 A1 | 4/2006 | Brown |
| 2006/0080819 A1 | 4/2006 | McAllister |
| 2006/0097875 A1 | 5/2006 | Ott |
| 2006/0171332 A1 | 8/2006 | Barnum |
| 2006/0192652 A1 | 8/2006 | Mandava |
| 2006/0238307 A1 | 10/2006 | Bauer |

(56) References Cited

U.S. PATENT DOCUMENTS

| | | |
|---|---|---|
| 2006/0244718 A1 | 11/2006 | Hiddink |
| 2007/0050070 A1 | 3/2007 | Strain |
| 2007/0050271 A1 | 3/2007 | Ufford |
| 2007/0064765 A1 | 3/2007 | Solie |
| 2007/0067177 A1 | 3/2007 | Martin |
| 2007/0067203 A1 | 3/2007 | Gil |
| 2007/0069867 A1 | 3/2007 | Fleisch |
| 2007/0076779 A1 | 4/2007 | Haarer |
| 2007/0156261 A1 | 7/2007 | Caldwell |
| 2007/0176773 A1 | 8/2007 | Smolander |
| 2007/0221727 A1 | 9/2007 | Reznik |
| 2008/0001752 A1 | 1/2008 | Bruns |
| 2008/0052201 A1 | 2/2008 | Bodin |
| 2008/0067227 A1 | 3/2008 | Poss |
| 2008/0073431 A1 | 3/2008 | Davis |
| 2008/0103944 A1 | 5/2008 | Hagemann |
| 2008/0186175 A1 | 8/2008 | Stern |
| 2008/0292759 A1 | 11/2008 | Palmer |
| 2008/0294488 A1 | 11/2008 | Gupta |
| 2009/0027213 A1 | 1/2009 | Debord |
| 2009/0040063 A1 | 2/2009 | Yearsley |
| 2009/0058644 A1 | 3/2009 | French |
| 2009/0076645 A1 | 3/2009 | Ben-Tzur |
| 2009/0083054 A1 | 3/2009 | Koo |
| 2009/0119170 A1 | 5/2009 | Hammad |
| 2009/0144122 A1 | 6/2009 | Ginsberg |
| 2009/0261974 A1 | 10/2009 | Bailey |
| 2009/0322481 A1 | 12/2009 | Marr, III |
| 2010/0006646 A1 | 1/2010 | Stiller |
| 2010/0007464 A1 | 1/2010 | McTigue |
| 2010/0042369 A1 | 2/2010 | Mian |
| 2010/0065632 A1 | 3/2010 | Babcock |
| 2010/0101317 A1 | 4/2010 | Ashrafzadeh |
| 2010/0138281 A1 | 6/2010 | Zhang |
| 2010/0253504 A1 | 10/2010 | Lliteras |
| 2011/0029413 A1* | 2/2011 | Ben-Tzur ............... G06Q 10/08 705/28 |
| 2011/0035326 A1 | 2/2011 | Sholl |
| 2011/0068921 A1 | 3/2011 | Shafer |
| 2011/0301903 A1 | 12/2011 | Humbert |
| 2012/0101876 A1 | 4/2012 | Turvey |
| 2012/0161967 A1 | 6/2012 | Stern |
| 2012/0264446 A1 | 10/2012 | Xie |
| 2012/0267541 A1 | 10/2012 | Utukuri |
| 2012/0304014 A1 | 11/2012 | Prophete |
| 2012/0310853 A1 | 12/2012 | Aldstadt |
| 2013/0002443 A1 | 1/2013 | Breed |
| 2013/0117053 A2 | 5/2013 | Campbell |
| 2013/0176115 A1 | 7/2013 | Puleston |
| 2013/0214797 A1 | 8/2013 | Gruden |
| 2013/0218511 A1 | 8/2013 | Mager |
| 2013/0235206 A1 | 9/2013 | Smith |
| 2013/0271290 A1* | 10/2013 | Saenz ..................... G05D 27/02 340/870.07 |
| 2013/0282522 A1 | 10/2013 | Hassan |
| 2014/0138440 A1 | 5/2014 | D'Ambrosio |
| 2014/0146164 A1 | 5/2014 | Bajema |
| 2014/0147015 A1 | 5/2014 | Bajema |
| 2014/0180953 A1 | 6/2014 | Westcott |
| 2014/0201041 A1 | 7/2014 | Meyer |
| 2014/0294239 A1 | 10/2014 | Duckett |
| 2014/0297487 A1 | 10/2014 | Bashkin |
| 2014/0313055 A1 | 10/2014 | Warkentin |
| 2014/0316875 A1 | 10/2014 | Tkachenko |
| 2014/0330407 A1 | 11/2014 | Corder |
| 2015/0015373 A1 | 1/2015 | Mongrenier |
| 2015/0019391 A1 | 1/2015 | Kumar |
| 2015/0021401 A1 | 1/2015 | Rajagopal |
| 2015/0022313 A1 | 1/2015 | Maier |
| 2015/0041616 A1 | 2/2015 | Gentile |
| 2015/0048938 A1 | 2/2015 | Tew |
| 2015/0084100 A1 | 3/2015 | Sablong |
| 2015/0095255 A1 | 4/2015 | Hall |
| 2015/0102903 A1 | 4/2015 | Wilkinson |
| 2015/0186840 A1 | 7/2015 | Torres |
| 2015/0192475 A1 | 7/2015 | Eisenstadt |
| 2015/0245179 A1 | 8/2015 | Jarvis |
| 2015/0338846 A1 | 11/2015 | Boivin |
| 2015/0347945 A1 | 12/2015 | Reese |
| 2015/0349917 A1 | 12/2015 | Skaaksrud |
| 2016/0012337 A1 | 1/2016 | Kaye |
| 2016/0026032 A1 | 1/2016 | Moore |
| 2016/0034907 A1 | 2/2016 | Worrall |
| 2016/0048798 A1 | 2/2016 | Meyer |
| 2016/0063367 A1 | 3/2016 | Cai |
| 2016/0132821 A1 | 5/2016 | Glasgow |
| 2016/0148440 A1 | 5/2016 | Kwak |
| 2016/0171434 A1 | 6/2016 | Ladden |
| 2016/0189087 A1 | 6/2016 | Morton |
| 2016/0203591 A1 | 7/2016 | Justaniah |
| 2016/0217417 A1 | 7/2016 | Ma |
| 2016/0239794 A9 | 8/2016 | Shafer |
| 2016/0260059 A1 | 9/2016 | Benjamin |
| 2016/0283904 A1 | 9/2016 | Siegel |
| 2016/0292634 A1 | 10/2016 | Mehring |
| 2016/0307040 A1 | 10/2016 | Shulman |
| 2016/0314514 A1 | 10/2016 | High |
| 2016/0350715 A1 | 12/2016 | Minvielle |
| 2016/0350756 A1 | 12/2016 | Shepard |
| 2017/0011276 A1* | 1/2017 | Mehring ............... G06K 9/4652 |
| 2017/0039194 A1 | 2/2017 | Tschetter |
| 2017/0039511 A1 | 2/2017 | Corona |
| 2017/0059391 A1 | 3/2017 | Ademe |
| 2017/0061171 A1 | 3/2017 | Lombardi |
| 2017/0074921 A1 | 3/2017 | Uota |
| 2017/0102694 A1 | 4/2017 | Enver |
| 2017/0116565 A1 | 4/2017 | Feiner |
| 2017/0122771 A1 | 5/2017 | Keal |
| 2017/0164773 A1 | 6/2017 | Wirtz |
| 2017/0255901 A1 | 9/2017 | Bermudez Rodriguez |
| 2017/0269601 A1 | 9/2017 | Jones |
| 2017/0280351 A1 | 9/2017 | Skaaksrud |
| 2017/0286905 A1 | 10/2017 | Richardson |
| 2017/0300984 A1 | 10/2017 | Hurwich |
| 2017/0322090 A1 | 11/2017 | Jones |
| 2017/0344934 A1 | 11/2017 | Millhouse |
| 2017/0344935 A1 | 11/2017 | Mattingly |
| 2018/0007453 A1 | 1/2018 | Taylor |
| 2018/0039853 A1 | 2/2018 | Liu |
| 2018/0045700 A1 | 2/2018 | Biermann |
| 2018/0078992 A1 | 3/2018 | High |
| 2018/0096175 A1 | 4/2018 | Schmeling |
| 2018/0137642 A1 | 5/2018 | Malisiewicz |
| 2018/0143131 A1 | 5/2018 | Choi |
| 2018/0144300 A1 | 5/2018 | Wiechers |
| 2018/0144430 A1 | 5/2018 | Millhouse |
| 2018/0150684 A1 | 5/2018 | Wang |
| 2018/0180492 A1 | 6/2018 | Ribi |
| 2018/0181838 A1 | 6/2018 | Yang |
| 2018/0195869 A1 | 7/2018 | High |
| 2018/0211208 A1 | 7/2018 | Winkle |
| 2018/0217118 A1 | 8/2018 | Payne |
| 2018/0242768 A1 | 8/2018 | Lewis |
| 2018/0247257 A1 | 8/2018 | Johng |
| 2018/0270631 A1 | 9/2018 | High |
| 2018/0279023 A1 | 9/2018 | Taylor |
| 2018/0290809 A1 | 10/2018 | Espinosa |
| 2018/0315011 A1 | 11/2018 | Clarke |
| 2018/0341905 A1 | 11/2018 | Johnsen |
| 2019/0073770 A1 | 3/2019 | Moradi |
| 2019/0147396 A1 | 5/2019 | Bohling |
| 2019/0223643 A1 | 7/2019 | Hara |
| 2019/0265082 A1* | 8/2019 | Zafar ..................... G01D 7/00 |
| 2019/0285603 A1 | 9/2019 | Velez |
| 2019/0295019 A1* | 9/2019 | Mehring ............... G06Q 10/08 |
| 2020/0034962 A1 | 1/2020 | Mathew |
| 2020/0085290 A1 | 3/2020 | Wang |
| 2020/0118072 A1 | 4/2020 | Johnson |
| 2020/0160497 A1 | 5/2020 | Shah |
| 2020/0242402 A1 | 7/2020 | Jung |
| 2020/0275010 A1 | 8/2020 | Bohling |

(56) References Cited

U.S. PATENT DOCUMENTS

| | | |
|---|---|---|
| 2021/0398065 A1 | 12/2021 | Johnsen |
| 2022/0010160 A1 | 1/2022 | Zhong |

FOREIGN PATENT DOCUMENTS

| | | |
|---|---|---|
| CN | 201314907 | 9/2009 |
| CN | 202306566 | 7/2012 |
| CN | 102930649 | 2/2013 |
| CN | 203275285 | 11/2013 |
| CN | 203306566 | 11/2013 |
| CN | 103543703 | 1/2014 |
| CN | 103593746 A | 2/2014 |
| CN | 104036354 | 9/2014 |
| CN | 204010264 | 12/2014 |
| CN | 104749329 A | 7/2015 |
| CN | 204514846 | 7/2015 |
| CN | 105444504 | 3/2016 |
| CN | 106408173 | 2/2017 |
| CN | 106600286 | 4/2017 |
| CN | 107703269 | 2/2018 |
| EP | 1221613 | 7/2002 |
| EP | 1374688 | 1/2004 |
| EP | 2165298 | 3/2010 |
| EP | 2509412 | 10/2012 |
| EP | 2509412 A1 | 10/2012 |
| EP | 2835078 | 2/2015 |
| GB | 2256708 | 12/1992 |
| JP | 2002195971 A | 7/2002 |
| JP | 2008004133 | 1/2008 |
| JP | 2008004133 A | 1/2008 |
| JP | 2013068547 | 4/2013 |
| WO | 2000078919 A1 | 12/2000 |
| WO | 2001023256 | 4/2001 |
| WO | 2003098175 | 11/2003 |
| WO | 2007052208 A1 | 5/2007 |
| WO | 2008006152 A1 | 1/2008 |
| WO | 2009147821 A1 | 12/2009 |
| WO | 2012125960 | 9/2012 |
| WO | 2013174983 | 11/2013 |
| WO | 2014059048 | 4/2014 |
| WO | 2015061429 | 4/2015 |
| WO | 2015066594 | 5/2015 |
| WO | 2020023762 | 1/2020 |

OTHER PUBLICATIONS

PCT; PCT App. No. PCT/US19/22699; International Search Report and Written Opinion dated Jul. 5, 2019.
3M; "3M MonitorMark Time Temperature Indicators"; https://www.3m.com/3M/en_US/company-us/all-3m-products/~/MONMARK-3M-MonitorMark-Time-Temperature-Indicators/?N=5002385+3293785721&rt=rud; Available at least as early as Feb. 7, 2019; pp. 1-4.
Agrofresh; "FreshCloud™ Storage Insights helps you monitor fruit in storage for added peace of mind"; https://www.agrofresh.com/technologies/freshcloud/storage-insights/; Available at least as early as Feb. 7, 2019; pp. 1-4.
Ahearn, Brianna; "Kroger Wins for Food Temperature Innovation"; https://www.retailsupplychaininsights.com/doc/kroger-wins-for-food-temperature-innovation-0001; Jun. 4, 2015; pp. 1-2.
Ambrosus; "Decentralised IoT Networks for Next-Generation Supply Chains"; https://ambrosus.com/#home; Available at least as early as Feb. 7, 2019; pp. 1-12.
BT9 Intelligent Supply Chain Solutions; "Multi Segment, Real Time, Cold Chain Perishable Information"; http://www.bt9-tech.com; Published 2018; pp. 1-6.
Business Wire; "Emerson Expands Global Capabilities in Fresh Food Monitoring with Acquisitions of Locus Traxx and PakSense"; https://www.businesswire.com/news/home/20160830005136/en/Emerson-Expands-Global-Capabilities-Fresh-Food-Monitoring; Aug. 30, 2016; pp. 1-2.
Cao, Jordan; "Intelligent Container—powered by SAP HANA"; https://blogs.saphana.com/2018/09/27/intelligent-container-powered-sap-hana/; Sep. 27, 2018; pp. 1-5.
Carrefour Group; "Carrefour launches Europe's first food blockchain"; http://www.carrefour.com/current-news/carrefour-launches-europes-first-food-blockchain; Mar. 6, 2018; pp. 1-2.
De Troch, Stefan; "Item-level cold chain monitoring, another cool NFC solution"; https://blog.nxp.com/internet-of-things-2/item-level-cold-chain-monitoring-another-cool-nfc-solution; Aug. 30, 2016; pp. 1-5.
Digi; "Digi Honeycomb Keeping food safe just got easier and cheaper. Digi Honeycomb lets you monitor your entire Cold Chain System"; https://s3.amazonaws.com/telusdigital-marketplace-production/iot/user-content/product/64aa-o.pdf; Available at least as early as Feb. 7, 2019; pp. 1-2.
Dji Ferntech; "Drones for Agriculture"; https://www.djistore.co.nz/agriculture; Available at least as early as Feb. 7, 2019; pp. 1-13.
Ecoark Holdings, Inc.; "Ocean Mist Farms Selects Zest Fresh to Optimize Freshness Management"; https://www.globenewswire.com/news-release/2018/12/04/1661680/0/en/Ocean-Mist-Farms-Selects-Zest-Fresh-to-Optimize-Freshness-Management.html; Dec. 4, 2018; pp. 1-3.
Emerson; "ProAct Services and ProAct Transport"; https://www.emerson.com/en-us/commercial-residential/proact; Available at least as early as Feb. 7, 2019; pp. 1-4.
Emerson; "Real-Time Temperature & Location Trackers"; https://climate.emerson.com/en-us/products/controls-monitoring-systems/cargo-tracking-monitoring/trackers; Available at least as early as Feb. 7, 2019; pp. 1-4.
Emerson; "Supply Chain Data Loggers"; https://climate.emerson.com/en-us/products/controls-monitoring-systems/cargo-tracking-monitoring/loggers; Available at least as early as Feb. 7, 2019; pp. 1-4.
Fast Casual; "Wireless temperature-monitoring, tracking solution available for shipping perishable goods"; https://www.fastcasual.com/news/wireless-temperature-monitoring-and-tracking-solution-now-available-for-shipping-perishable-goods/; Aug. 15, 2017; pp. 1-10.
Food and Agriculture Organization of the United Nations; "Flying robots for food security"; http://www.fao.org/zhc/detail-events/en/c/428256; Aug. 10, 2016; pp. 1-3.
Freshai; "AI-powered waste reduction for smart food businesses."; http://freshai.farmsteadapp.com/; Available as early as Feb. 7, 2019; pp. 1-5.
freshfruitportal.com; "Zest Labs fights food waste by routing pallets according to real-time freshness"; https://www.freshfruitportal.com/news/2018/07/19/technology-zest-labs-food-waste-profits-sensors; Jul. 19, 2018; pp. 1-5.
Friedman, Phil; "AI, machine learning, and more efficient routing"; https://www.omnitracs.com/blog/ai-machine-learning-and-more-efficient-routing; Jun. 28, 2018; pp. 1-6.
Gabbett, Rita Jane; "Amazon using artificial intelligence to monitor food safety issues"; http://www.micausa.org/amazon-using-artificial-intelligence-monitor-food-safety-issues/; May 9, 2018; pp. 1-3.
Grand View Research; "Cold Chain Market Size Worth $447.50 Billion by 2025 | CAGR: 15.1%"; https://www.grandviewresearch.com/press-release/global-cold-chain-market; Mar. 2019; pp. 1-10.
Greenwalt, Megan; "Acquisition Leads to New, Fresh Food Waste Solution"; https://www.waste360.com/mergers-and-acquisitions/acquisition-leads-new-fresh-food-waste-solution; Aug. 15, 2018; pp. 1-6.
Hagen, Christian et al.; "A Fresh Look: Perishable Supply Chains Go Digital"; https://www.atkearney.com/operations-performance-transformation/article?/a/a-fresh-look-perishable-supply-chains-go-digital; Available at least as early as Feb. 7, 2019; pp. 1-22.
Harvard Business Review; "How Blockchain Will Accelerate Business Performance and Power the Smart Economy"; https://hbr.org/sponsored/2017/10/how-blockchain-will-accelerate-business-performance-and-power-the-smart-economy; Oct. 27, 2017; pp. 1-8.
Hsu, Jenny W.; "Freshippo Customers Can Track Farm-To-Shelf Journey for Food"; https://www.alizila.com/hema-food-tracking/; Aug. 7, 2018; pp. 1-6.

(56) References Cited

OTHER PUBLICATIONS

Husseini, Talal; "Walmart's 'Eden' artificial intelligence technology to inspect fresh food for spoilage"; https://www.foodprocessing-technology.com/news/walmarts-eden-artificial-intelligence-technology-inspect-fresh-food-spoilage; Mar. 2, 2018; pp. 1-4.
IBM; "Take your food data further with Fresh Insights for IBM Food Trust"; https://www.ibm.com/blockchain/solutions/food-trust/freshness; Available at least as early as Feb. 7, 2019; pp. 1-3.
Impact Vision; "Non-invasive, real time food quality information"; https://www.impactvi.com/; Available at least as early as Feb. 7, 2019; pp. 1-18.
Impinj; "Hy-Vee Grocery Automates Cold Chain Monitoring"; https://www.impinj.com/library/customer-stories/hy-vee-cold-chain-monitoring-increases-shelf-life/; Available as early as Feb. 7, 2019; pp. 1-3.
INFRATAB; "Products"; https://infratab.com/products/; Available at least as early as Feb. 7, 2019; pp. 1-2.
Intel; "Intelligent Dynamic Store Merchandising Solution Cuts Losses on Perishables and Raises Brand Awareness"; Available at least as early as Feb. 7, 2019; pp. 1-12.
Kroger; "Kroger Gets HarvestMark Allows consumers to trace the origin of salads"; https://www.cspdailynews.com/foodservice/kroger-gets-harvestmark; Oct. 29, 2009; pp. 1-11.
Marvin, Rob; "Blockchain: The Invisible Technology That's Changing the World"; https://in.pcmag.com/amazon-web-services/112363/blockchain-the-invisible-technology-thats-changing-the-world; Aug. 30, 2017; pp. 1-29.
Mazur, Michal; "Six Ways Drones Are Revolutionizing Agriculture"; https://www.technologyreview.com/s/601935/six-ways-drones-are-revolutionizing-agriculture; Jul. 20, 2016; pp. 1-5.
Moorthy, Rahul et al.; "On-Shelf Availability in Retailing"; vol. 116—No. 23; International Journal of Computer Applications; Apr. 2015; pp. 47-51.
Musani, Parvez; "Eden: The Tech That's Bringing Fresher Groceries to You"; https://blog.walmart.com/innovation/20180301/eden-the-tech-thats-bringing-fresher-groceries-to-you; Mar. 1, 2018; pp. 1-4.
My Devices; "Alibaba Cloud and myDevices Partner to Launch Turnkey IoT Solutions in China"; https://mydevices.com/newspost/alibaba-cloud-mydevices-partner-launch-turnkey-iot-solutions-china/; Sep. 11, 2018; pp. 1-3.
Oracle; "Oracle Unveils Business-Ready Blockchain Applications"; https://www.oracle.com/nz/corporate/pressrelease/oow18-oracle-blockchain-applications-cloud-2018-10-23.html; Oct. 23, 2018; pp. 1-4.
Palanza, Rich; "IoT Monitoring: Rapidly Deliver on the Promise of IoT"; https://business.weather.com/blog/iot-monitoring-rapidly-deliver-on-the-promise-of-iot; May 16, 2018; pp. 1-4.
Peterson, Hayley; "Walmart is saving $2 billion with a machine called 'Eden' that inspects food and knows when it will spoil"; https://www.businessinsider.in/walmart-is-saving-2-billion-with-a-machine-called-eden-that-inspects-food-and-knows-when-it-will-spoil/articleshow/63127641.cms; Mar. 1, 2018; pp. 1-12.
Pridevel; "IoT Cold Chain Monitoring"; http://www.pridevel.com/sap-iot-cold-chain-monitoring; Available at least as early as Feb. 7, 2019; pp. 1-3.
QA; "Carrefour and SGS Launch Visual Trust in China"; https://www.qualityassurancemag.com/article/carrefour-and-sgs-launch-visual-trust-in-china/; Sep. 28, 2017; pp. 1-4.
Ripple News Tech Staff; "Alibaba is Using Blockchain to Improve Consumer Confidence and Fight Food Fraud"; https://ripplenews.tech/2018/05/03/alibaba-is-using-blockchain-to-improve-consumer-confidence-and-fight-food-fraud/; May 3, 2018; pp. 1-7.
Sensefly; "Why Use Agriculture Drones?"; https://www.sensefly.com/industry/agricultural-drones-industry; Available at least as early as Feb. 7, 2019; pp. 1-15.
Sensegrow; "Supply Chain Monitoring with Real-time IoT Platform"; http://www.sensegrow.com/blog/supply-chain-monitoring; May 10, 2018; pp. 1-5.
Smart Sense; "Supermarket Remote Monitoring Solutions"; https://www.smartsense.co/industries/retail/supermarkets; Available at least as early as Feb. 7, 2019; pp. 1-6.
Smilo; "The latest generation hybrid blockchain platform"; https://smilo.io/files/Smilo_White_Paper_V1.8.1.pdf; Available at least as early as Feb. 7, 2019; pp. 1-33.
Springer, Jon; "Walmart, Kroger join suppliers in blockchain food safety initiative"; https://www.supermarketnews.com/news/walmart-kroger-join-suppliers-blockchain-food-safety-initiative; Aug. 22, 2017; pp. 1-4.
TCS Worldwide; "TCS Cargo Monitoring Solution: Track freshness of perishable cargo"; https://www.tcs.com/cargo-monitoring-solution; Available at least as early as Feb. 7, 2019; pp. 1-7.
TE-Food; "TE-Food Partners with Halal Trail Bringing Halal Food Companies to the Blockchain"; https://www.reuters.com/brandfeatures/venture-capital/article?id=38153; May 31, 2018; pp. 1-6.
Tech Mahindra; "Cold Chain Monitoring"; https://www.techmahindra.com/services/NextGenSolutions/DES/Solutions/Cold_Chain_Monitoring.aspx; Available at least as early as Feb. 7, 2019; pp. 1-4.
Tech Mahindra; "Farm to fork"; https://www.techmahindra.com/services/NextGenSolutions/DES/Solutions/Farm_to_fork.aspx; Available at least as early as Feb. 7, 2019; pp. 1-2.
Tive; "A Complete Supply Chain Visibility System"; https://tive.co/product; Available at least as early as Feb. 7, 2019; pp. 1-7.
Tive; "Environmental Monitoring for Perishables"; https://tive.co/solution/environmental-monitoring-for-perishables/; Available at least as early as Feb. 7, 2019; pp. 1-5.
Traqtion; "TraQtion's Supply Chain Solution Manages Global Food Supplier Compliance and Audits"; https://www.traqtion.com/documents/TraQtion-Costco.pdf; Available as early as Feb. 7, 2019; pp. 1-2.
Trimble; "Trimble Acquires HarvestMark to Provide Food Traceability and Quality Control"; https://www.prnewswire.com/news-releases/trimble-acquires-harvestmark-to-provide-food-traceability-and-quality-control-300070050.html; Apr. 22, 2015; pp. 1-6.
Tsenso; "The Fresh Index: A Real-Time Shelf Life Indicator"; https://tsenso.com/en/freshindex-instead-of-bestbefore; Available at least as early as Feb. 7, 2019; pp. 1-5.
Verigo; "Introducing Pod Quality Continuous Product Life Data, From Farm to Store"; https://www.farmtoforkfresh.com/; Available at least as early as Feb. 7, 2019; pp. 1-8.
Wageningen UR Food & Biobased Research; "Food & Biobased Research"; https://www.worldfoodinnovations.com/userfiles/documents/FBR%20Corporate%20Brochure.pdf; Jul. 2014; pp. 1-24.
Whelan, Jenny; "Kelsius to Install FoodCheck Monitoring System in SuperValu and Centra Stores"; https://www.checkout.ie/kelsius-signs-deal-to-put-foodcheck-monitoring-system-in-supervalu-and-centra-stores/; Aug. 6, 2015; pp. 1-4.
Wynne-Jones, Stephen; "Maxima Group Unveils 'Electronic Nose' to Track Freshness"; https://www.esmmagazine.com/maxima-group-unveils-elecrtronic-nose-track-freshness/29589; Jul. 5, 2016; pp. 1-4.
Xinfin; "Enterprise Ready Hybrid Blockchain for Global Trade and Finance"; https://www.xinfin.org; Available at least as early as Feb. 7, 2019; pp. 1-13.
Yiannas, Frank; "How Walmart's SPARK Keeps Your Food Fresh"; https://blog.walmart.com/sustainability/20150112/how-walmarts-spark-keeps-your-food-fresh; Jan. 12, 2015; pp. 1-16.
Zest Labs; "Zest Fresh for Growers, Retailers and Restaurants"; https://www.zestlabs.com/zest-fresh-for-produce/; Available at least as early as Feb. 7, 2019; pp. 1-7.
U.S. Appl. No. 16/112,974, filed Aug. 27, 2018, Joshua Bohling.
Bedard, Jean; "Temperature Mapping of Storage Areas"; Technical supplement to WHO Technical Report Series, No. 961, 2011; WHO Press, World Health Organization; available at least as early as Jan. 2014; pp. 1-25.
compact.net; "Inspection Planning / Quality Inspection / SPC / LIMS"; https://www.caq.de/en/Software/InspectionPlanning_QualityInspection_SPC; available at least as early as Jan. 27, 2017; pp. 1-4.
Eom, Ki-Hwan, et al.; "The Meat Freshness Monitoring System Using the Smart RFID Tag"; International Journal of Distributed

(56) References Cited

OTHER PUBLICATIONS

Sensor Networks, vol. 2014; http://journals.sagepub.com/doi/10.1155/2014/591812; Jul. 9, 2014; pp. 1-10.
Greis, Noel P.; "Monitoring the 'Cool Chain' Maximizing Shelf Life for Safer Food"; https://atecentral.net/r20093/case_study_monitoring_the_cool_chain; National Science Foundation; published on Dec. 2011; pp. 1-9.
IQA Team; "Material Inspection Using a Cloud Software"; http://Mqalims.com/wp-content/uploads/2015/02/MAT_INSP.pdf; available at least as early as Jan. 27, 2017; pp. 1-5.
Jedermann, Reiner, et al.; "Semi-passive RFID and Beyond: Steps Towards Automated Quality Tracing in the Food Chain"; Inderscience Enterprises Ltd.; Int. J. Radio Frequency Identification Technology and Applications, vol. 1, No. 3; published in 2007; pp. 247-259.
MIPSIS; "Quality Control Inspection Software"; http://www.mipsis.com/QualityInspectionSoftware.html; available at least as early as Jan. 27, 2017; pp. 1-3.
Moorthy, Rahul, et al.; "On-Shelf Availability in Retailing"; vol. 116—No. 23; International Journal of Computer Applications; available at least as early as Apr. 2015; pp. 47-51.
QC One; "Inspect. Report. Analyze. Quality Control Software for Fresh Produce"; http://qcone.com/en/; available at least as early as May 29, 2017; pp. 1-2.
Ryan, John M.; "Guide to Food Safety and Quality During Transportation: Controls, Standards and Practices"; Academic Press; available at least as early as 2014; pp. 1-8.
Softexpert; "SE Inspection Incoming/Outgoing Goods Inspection and Supplier Management"; https://softexpert.com/inspection-evaluation-goods.php; available at least as early as Jan. 27, 2017; pp. 1-3.
Yan, Lu, et al.; "The Internet of Things: From RFID to the Next-Generation Pervasive Networked Systems"; Auerbach Publications; New York; available at least as early as 2008; pp. 1-35.
Teijin—Human Chemistry, Human Solutions, Teijin's RFID Smart Shelf-Management System Used for Mass Document Management. Retrieved online at: http://www.teijin.com/news/2014/ebd140307_11.html. 2 pages, Mar. 7, 2014.
The NeWave® Smart Inventory Managment System: Take Your Management to the Next Level, NeWave Sensor Solutions Innovation Center, Oct. 7, 2016; pp. 1-2.
U.S. Appl. No. 16/526,677, filed Jul. 30, 2019, Bohling Joshua.
Arah, Isaac Kojo et al.; "Preharvest and Postharvest Factors Affecting the Quality and Shelf Life of Harvested Tomatoes: A Mini Review"; http://downloads.hindawi.com/journals/ija/2015/478041.pdf; Available as early as Oct. 14, 2015; pp. 1-7.
Badia, Ricardo; "Cold Chain Logistics: Assessing the Challenge"; https://www.zestlabs.com/assessing-cold-chain-logistics/; Mar. 19, 2019; pp. 1-4.
Barthe, J.F.; "D.2.3.2. Database of consumer awareness, expectations and concerns on cold chain"; http://www.frisbee-project.eu/images/result/FRISBEE_DEL_2-3-2.pdf; Dec. 2, 2011; pp. 1-26.
Barthe, J.F.; "D.2.3.2.1 Survey questionnaires and materials for studies of consumer perspectives and attitudes towards refrigerated foods, the cold chain and relevant refrigeration technologies (Informed consent forms, privacy, personal data handling)"; http://www.frisbee-project.eu/images/result/FRISBEE_DEL_2-3-2-1.pdf; Feb. 8, 2012; pp. 1-21.
Bevan et al.; "Storage of Organically Produced Crops"; https://orgprints.org/8241/1/Storage_organic_produce_report.pdf; Dec. 1997; pp. 1-227.
Bogataj, M., et al.; "Stability of perishable goods in cold logistic chains"; International Journal of Production Economics, vol. 93-94; 2005; pp. 345-356.
Capgemini; "Schuitema Revolutionizes Food Quality Control Through RFID"; https://www.capgemini.com/se-en/wp-content/uploads/sites/29/2017/07/Schuitema_Revolutionizes_Food_Quality_Control_Through_RFID.pdf; Jul. 29, 2017; pp. 1-2.
Chainlink Research; "Achieving Consistent Product Quality"; https://www.zestlabs.com/wp-content/uploads/2016/12/Quality-Management-For-Produ ce.pdf; Available as early as Dec. 2016; pp. 1-8.
Chainlink Research; "Measuring Produce Freshness: The Key to Preventing Waste"; https://www.zestlabs.com/wp-content/uploads/2016/03/Measuring-Produce-Freshness. pdf; Available as early as Mar. 2016; pp. 1-12.
Chainlink Research; "Preemptive Freshness Management"; https://www.zestlabs.com/wp-content/uploads/2017/03/Preemptive-Freshness-Managem ent.pdf; Available as early as Mar. 2017; pp. 1-8.
Chainlink Research; "Blockchain's Role in the Produce Supply Chain"; https://www.zestlabs.com/wp-content/uploads/2018/01/Blockchains-Role-in-the-Prod uce-Supply-Chain.pdf; Available as early as Jan. 2018; pp. 1-20.
Chainlink Research; "Pallet-level Monitoring"; https://www.zestlabs.com/wp-content/uploads/2016/03/Pallet-Monitoring-for-the-Fr esh-Food-Supply-Chain.pdf; Available as early as Mar. 2016; pp. 1-9.
Chainlink Research; "Why Quality Consistency Matters"; https://www.zestlabs.com/wp-content/uploads/2016/03/Why-Food-Supply-Chain-Qualit y-Matters-1.pdf; Available as early as Mar. 2016; pp. 1-10.
Claussen, Ingrid C.; "Deliverable D.3.2.4.3 Literature review and experimental data of chilled, superchilled/supercooled fish quality and safety models"; http://www.frisbee-project.eu/images/result/FRISBEE_DEL_3-2-4-3.pdf; May 6, 2011; pp. 1-29.
Colmer, Christian; "Chill—On! Transparent food quality all the way"; https://www.innovations-report.com/html/reports/medicine-health/chill-transparen t-food-quality-168201.html; Oct. 1, 2011; pp. 1-5.
Cotillon, C.; "Deliverable 8.2.1.1 Publication in Scientific Journals"; http://www.frisbee-project.eu/images/result/FRISBEE_DEL_8.2.1.1.pdf; Oct. 27, 2011; pp. 1-5.
Cotillon, C.; "Deliverable 8.3.3.1 Mini conferences"; http://www.frisbee-project.eu/images/result/FRISBEE_DEL_8.3.3.1.pdf; Dec. 7, 2011; pp. 1-8.
Cotillon, C.; "Deliverable 8.6.1 Report on collaboration with other EU projects"; http://www.frisbee-project.eu/images/result/FRISBEE_DEL_8.6.1.pdf; Dec. 5, 2011; pp. 1-12.
Dada, Ali, et al.; "Sensor Applications in the Supply Chain: The Example of Quality-Based Issuing of Perishables"; The Internet of Things. Lecture Notes in Computer Science, edited by Christian Floerkemeier, et al.; vol. 4952; 2008; pp. 140-154.
Desmedt, Frederique; "Deliverable 8.1.1 Project logo, Leaflet and PowerPoint presentation"; http://www.frisbee-project.eu/images/result/FRISBEE_DEL_8.1.1.pdf; Nov. 19, 2010; pp. 1-30.
Desmedt, Frederique; "Deliverable 8.1.2 Project internet and intranet website"; http://www.frisbee-project.eu/images/result/FRISBEE_DEL_8.1.2.pdf; Mar. 3, 2011; pp. 1-9.
Do Nascimento Nunes, M. C., et al.; "Improvement in fresh fruit and vegetable logistics quality: berry logistics field studies"; Philosophical Transactions of the Royal Society; http://dx.doi.org/10.1098/rsta.2013.0307; 2014; pp. 1-19.
Doyle, John P.; "Seafood Shelf Life as a Function of Temperature"; Alaska Sea Grant Marine Advisory Program; No. 30; 1989; pp. 1-6.
Evans, J.; "Deliverable D2.2.2 : Assessment of current refrigeration technologies of selected food industries and their potential improvement in current refrigeration"; http://www.frisbee-project.eu/images/result/FRISBEE_DEL_2-2-2.pdf; Jan. 30, 2012; pp. 1-181.
Evans, Judith et al.; "Deliverable D.2.2.3 : Analysis of potential of novel refrigeration technologies suitable for selected industries for application and improvement of food quality, energy consumption and environmental impact"; http://www.frisbee-project.eu/images/result/FRISBEE_DEL_2-2-3.pdf; Dec. 2, 2011; pp. 1-54.
Friedlos, Dave; "New Zealand Kiwifruit Processor Finds ROI"; https://www.rfidjournal.com/articles/view?4090; May 20, 2008; pp. 1-4.
Frisbee; "Frisbee european project—Archive"; https://web.archive.org/web/20180815100417/http://www.frisbee-project.eu/archive -results.html; Available as early as Aug. 15, 2018; pp. 1-5.
Frisbee; "Frisbee european project—Developing novel breakthrough technologies"; https://web.archive.org/web/20180316101206/http://www.frisbee-project.eu/researc h/92-developing-novel-breakthrough-technologies.html; Available as early Mar. 16, 2018; pp. 1-3.

(56) References Cited

OTHER PUBLICATIONS

Frisbee; "Frisbee european project—Frisbee at the Sixteenth Conference on Food Microbiology, Belgium"; http://www.frisbee-project.eu/news/40-frisbee-at-the-sixteenth-conference-on-foo d-microbiology.html; Nov. 15, 2011; pp. 1-1.
Frisbee; "Frisbee european project—Frisbee develops a Virtual Platform application"; http://www.frisbee-project.eu/news/90-frisbee-develops-a-virtual-platform-applic ation.html; Mar. 18, 2013; pp. 1-1.
Frisbee; "Frisbee european project—Frisbee dissemination activities"; http://www.frisbee-project.eu/news/91-frisbee-dissemination-activities.html; Mar. 18, 2013; pp. 1-1.
Frisbee; "Frisbee european project—Frisbee on the starting-blocks"; http://www.frisbee-project.eu/news/49-frisbee-on-the-starting-blocks.html; Mar. 9, 2012; pp. 1-2.
Frisbee; "Frisbee european project—Frisbee welcomes New Members Advisory Board"; http://www.frisbee-project.eu/news/48-new-members-advisory-board.html; Mar. 9, 2012; pp. 1-1.
Frisbee; "Frisbee european project—Frisbee: Latest Developments"; http://www.frisbee-project.eu/news/42-frisbee-project-latest-developments.html; Dec. 21, 2011; pp. 1-2.
Frisbee; "Frisbee european project—Join the first European Food Cold Chain Database!!!";http://www.frisbee-project.eu/news/55-database2.html; Jul. 9, 2012; pp. 1-2.
Frisbee; "Frisbee european project—Magnetic refrigeration technology. Frisbee's experts team work on this disruptive technology"; https://web.archive.org/web/20180316101206/http://www.frisbee-project.eu/researc h/51-magnetic-refrigeration-technology.html; Available as early as Mar. 16, 2018; pp. 1-3.
Frisbee; "Frisbee european project—MEP-scientist pairing scheme"; http://www.frisbee-project.eu/news/41-mep-scientist-pairing-scheme.html; Dec. 20, 2011; pp. 1-2.
Frisbee; "Frisbee european project—Nanoparticles, a concentrate of energy: PCM nanoparticles where low temperatures are needed"; https://web.archive.org/web/20180316101206/http://www.frisbee-project.eu/researc h/27-nanoparticles-a-concentrate-of-energy.html; Available as early as Mar. 16, 2018; pp. 1-2.
Frisbee; "Frisbee european project—Project Overview"; https://web.archive.org/web/20120211082956/http://www.frisbee-project.eu/project -overview.html; Available as early as Feb. 11, 2012; pp. 1-1.
Frisbee; "Frisbee european project—Saving energy by refrigeration predictive control"; https://web.archive.org/web/20180316101206/http://www.frisbee-project.eu/researc h/52-saving-energy-by-refrigeration-predictive-control.html; Available as early as Mar. 16, 2018; pp. 1-3.
Frisbee; "Frisbee european project—Superchilling! A new technology to have your food products fresher than fresh"; https://web.archive.org/web/20180316101206/http://www.frisbee-project.eu/researc h/50-superchilling.html; Available as early as Mar. 16, 2018; pp. 1-3.
Frisbee; "Frisbee european project—Taking Europe's temperature: Cold chain database"; http://www.frisbee-project.eu/news/89-taking-europe%E2%80%99s-temperature-cold-c hain-database.html; Mar. 18, 2013; pp. 1-2.
Frisbee; "Frisbee european project—Workpackages"; https://web.archive.org/web/20120210124516/http://www.frisbee-project.eu/workpac kages.html; Available as early as Feb. 10, 2012; pp. 1-2.
Frisbee; "Simulate a cold chain"; https://frisbee-etool.irstea.fr; Available as early as 2020; pp. 1-3.
Gapud, Veny; "Food Safety Trends Exploring Implications of Mandatory Safety Standards in Retail and Foodservice"; https://www.foodsafetymagazine.com/magazine-archive1/december-2009january-2010/f ood-safety-trends-exploring-implications-of-mandatory-safety-standards-in-retail -and-foodservice/; Dec. 12, 2019; pp. 1-20.
Gaukler, Gary et al.; "Establishing Dynamic Expiration Dates for Perishables: An Application of RFID and Sensor Technology"; International Journal of Production Economics; vol. 193; Jul. 25, 2017; pp. 617-632.

GEIE/CEMA/ITP; "Deliverable D 8.3.1.3 Newsletter edited by GEIE for industrial use N°3"; http://www.frisbee-project.eu/images/result/FRISBEE_DEL_8.3.1.3.pdf; Mar. 13, 2012; pp. 1-10.
GEIE/CEMA/ITP; "Deliverable D8.3.1.2 Newsletter edited by GEIE for industrial use N°2"; http://www.frisbee-project.eu/images/result/FRISBEE_DEL_8.3.1.2.pdf; Oct. 27, 2011; pp. 1-10.
Giannakourou, M. C., et al.; "Application of a TTI-Based Distribution Management System for Quality Optimization of Frozen Vegetables at the Consumer End"; Journal of Food Science, vol. 68, Issue 1; Jan. 2003; pp. 201-209.
Hertog, M. L. A. T. M., et al.; "Shelf-life modelling for first-expired-first-out warehouse management"; Philosophical Transactions of the Royal Society; http://dx.doi.org/10.1098/rsta.2013.0306; 2014; pp. 1-15.
IBM; "DHL Breaks New Ground with RFID-Based Real-Time Tracking of Sensitive Shipments"; ftp://ftp.software.ibm.com/software/solutions/pdfs/ODC00298-USEN-00.pdf; Available as early as Mar. 2007; pp. 1-4.
IBM; "Focus on Food Safety"; https://www.ibm.com/downloads/cas/ZN9EWKRQ; Available at least as early as 2018; pp. 1-2.
Infratab; "Infratab Freshtime RF Sensor Blockchain Solutions for the Fresh Seafood Cold Chain"; https://web.aimglobal.org/external/wcpages/wcecommerce/eComItemDetailsPage.aspx?ItemID=656; 2019; pp. 1-5.
Jedermann, Reiner, et al.; "Communication techniques and challenges for wireless food quality monitoring"; Philosophical Transactions of the Royal Society; http://dx.doi.org/10.1098/rsta.2013.0304; 2014; pp. 1-18.
Jedermann, Reiner, et al.; "Reducing food losses by intelligent food logistics"; Philosophical Transactions of the Royal Society; http://dx.doi.org/10.1098/rsta.2013.0302; 2014; pp. 1-20.
Kader, A. A.; "Pre- and Postharvest Factors Affecting Fresh Produce Quality, Nutritional Value, and Implications for Human Health"; Proceedings of the International Congress of Food Production and the Quality of Life, Sassari (Italy) Sep. 4-8, 2000, vol. 1, pp. 109-119.
Ketzenberg, M., et al.; "Expiration Dates and Order Quantities for Perishables"; European Journal of Operational Research; vol. 266, Issue 2; Apr. 2018; pp. 569-584.
Ketzenberg, M., et al.; "Managing Perishables with Time and Temperature History"; Production and Operations Management; vol. 24, Issue 1; Jan. 2015; pp. 54-70.
Ketzenberg, M., et al.; "The Value of RFID Technology Enabled Information to Manage Perishables"; https://pdfs.semanticscholar.org/bded/16af2e689b4fdcea7f8421f6e012a6041324.pdf; Apr. 2009; pp. 1-37.
Koutsoumanis, K., et al.; "Development of a safety monitoring and assurance system for chilled food product"; International Journal of Food Microbiology, vol. 100; 2005; pp. 253-260.
Leake, Linda L.; "The Search for Shelf Life Solutions"; https://www.ift.org/news-and-publications/food-technology-magazine/issues/2007/n ovember/columns/laboratory?page=viewall; Nov. 1, 2007; pp. 1-8.
McBeath, Bill; "Winning the Freshness Wars: Creating Shopper Loyalty and Improving Profitability in Retail Grocery"; https://www.zestlabs.com/wp-content/uploads/2016/11/ZL_WP_FreshnessWars_060415.p df; Available as early as Feb. 2013; pp. 1-16.
Mehring, Peter; "Blockchain for Food Safety—Addressing the Challenges"; https://www.zestlabs.com/will-blockchain-solve-food-safety-challenges/; Sep. 26, 2018; pp. 1-4.
Mehring, Peter; "Zest Labs CEO Peter Mehring on the Walmart Lawsuit"; https://www.zestlabs.com/zest-labs-ceo-peter-mehring-walmart-lawsuit/; Aug. 1, 2018; pp. 1-4.
Mitrokotsa et al.; "Integrated RFID and Sensor Networks: Architectures and Applications"; https://pdfs.semanticscholar.org/e5b0/c2a44971bad209cbf66afb6c825f89792723.pdf; Jun. 22, 2009; pp. 511-536.
NBC Bay Area; "Tech Company Helps Inspect Food During Shutdown"; https://www.nbcbayarea.com/news/tech/tech-company-helps-inspect-food-during-shut down_bay-area/4851; Jan. 11, 2019; pp. 1-6.

(56) References Cited

OTHER PUBLICATIONS

NRDC; "Wasted: How America is Losing up to 40 Percent of Its Food From Farm to Fork Landfill"; https://www.nrdc.org/sites/default/files/wasted-2017-report.pdf; Available as early as Aug. 2017; pp. 1-58.

Opatova, H.; "Deliverable 8.2.2.1 Organisation of a Workshop in Prague 2011 at International Congress of Refrigeration"; http://www.frisbee-project.eu/images/result/FRISBEE_DEL_8.2.2.1.pdf; Oct. 27, 2011; pp. 1-8.

Payne, Kevin; "New Verizon Ad Sheds Light on Important Food Safety Issues"; https://www.zestlabs.com/new-verizon-ad-sheds-light-on-important-food-safety-iss ues/; Dec. 15, 2017; pp. 1-4.

Payne, Kevin; "Agriculture Technology and "The Messy Middle""; https://www.zestlabs.com/agriculture-technology-messy-middle/; Jun. 25, 2019; pp. 1-4.

Payne, Kevin; "Are You Ready to Make 2018 Your Best Year Ever?" https://www.zestlabs.com/are-you-ready-to-make-2018-your-best-year-ever/; Feb. 13, 2018; pp. 1-4.

Payne, Kevin; "Blockchain for Fresh Food Supply Chains—Reality Sets In?"; https://www.zestlabs.com/blockchain-fresh-supply-chains-reality/; May 7, 2019; pp. 1-4.

Payne, Kevin; "Cold Chain Visibility: Who's Winning the Freshness Wars?"; https://www.zestlabs.com/cold-chain-visibility-freshness-wars/; Apr. 9, 2019; pp. 1-4.

Payne, Kevin; "Cold Supply Chain Variability—The Impact of Delays"; https://www.zestlabs.com/cold-supply-chain-variability/; Apr. 23, 2019; pp. 1-4.

Payne, Kevin; "Earth Day 2019 and Looking Ahead to 2020"; https://www.zestlabs.com/earth-day-2019/; Apr. 30, 2019; pp. 1-4.

Payne, Kevin; "Finding the Right Tools: Can Blockchain and IOT Fix the Fresh Food Supply Chain?—Register for the Webinar"; https://www.zestlabs.com/finding-the-right-tools-can-blockchain-and-iot-fix-the- fresh-food-supply-chain-register-for-the-webinar/; Feb. 27, 2018; pp. 1-4.

Payne, Kevin; "Food Grower and Supplier Challenges: The Top 10"; https://www.zestlabs.com/food-growers-suppliers-challenges/; Feb. 19, 2019; pp. 1-4.

Payne, Kevin; "Food Labels and Food Waste—A Solution"; https://www.zestlabs.com/food-labels-food-waste/; Mar. 12, 2019; pp. 1-4.

Payne, Kevin; "Food Safety Tips: Three Things to Consider"; https://www.zestlabs.com/food-safety-tips-three-things-to-consider/; Jul. 2, 2019; pp. 1-4.

Payne, Kevin; "Fresh Produce and Health: What's the Connection?"; https://www.zestlabs.com/fresh-produce-health-interrelationship/; Apr. 2, 2019; pp. 1-4.

Payne, Kevin; "Grocery Shopper Trends 2019: Key Insights"; https://www.zestlabs.com/grocery-shopper-trends-2019-key-insights/; Jul. 23, 2019; pp. 1-4.

Payne, Kevin; "How to Feed a Hungry Planet: Food for Thought"; https://www.zestlabs.com/feed-a-hungry-planet/; Aug. 6, 2019; pp. 1-4.

Payne, Kevin; "Hyped Up? Blockchain and Why a Hybrid Model is Best"; https://www.zestlabs.com/hyped-up-blockchain-the-fresh-food-supply-chain-and-why -a-hybrid-model-is-best/; Jan. 30, 2018; pp. 1-4.

Payne, Kevin; "I'll Never Look at Strawberries the Same Way"; https://www.zestlabs.com/ill-never-look-at-strawberries-the-same-way/; Dec. 15, 2017; pp. 1-4.

Payne, Kevin; "Improving Operational Efficiency: TQM for the Fresh Food Supply Chain"; https://www.zestlabs.com/improving-operational-efficiency-deming-drucker/; Aug. 27, 2019; pp. 1-4.

Payne, Kevin; "Increasing Trucking Costs Further Squeezes Grocery Margins—Don't Waste Your Money!" https://www.zestlabs.com/increasing-trucking-costs-further-squeezes-grocery-marg ins-dont-waste-your-money/; Feb. 6, 2018; pp. 1-4.

Payne, Kevin; "IoT Sensors and Reducing Food Waste"; https://www.zestlabs.com/iot-sensors-reduce-food-waste/; Feb. 12, 2019; pp. 1-4.

Payne, Kevin; "Millennials Want True Transperency"; https://www.zestlabs.com/millennials-want-true-transparency/; Jan. 9, 2018; pp. 1-4.

Payne, Kevin; "Myth Busting: Produce Shrink is Caused at the Store"; https://www.zestlabs.com/myth-busting-produce-shrink-occurs-at-the-store/; Feb. 20, 2018; pp. 1-4.

Payne, Kevin; "New Zest Fresh for Produce Modules: Rapid Implementations and Faster ROI"; https://www.zestlabs.com/zest-fresh-produce-modules/; Jul. 10, 2019; pp. 1-4.

Payne, Kevin; "Online Grocery Shopping Options Abound But . . . "; https://www.zestlabs.com/online-grocery-shopping/; Feb. 5, 2019; pp. 1-4.

Payne, Kevin; "Preventing Food Waste: Multiple Approaches"; https://www.zestlabs.com/preventing-food-waste-multiple-approaches/; Jul. 16, 2019; pp. 1-4.

Payne, Kevin; "Proactive Food Safety: Moving the Industry Forward"; https://www.zestlabs.com/proactive-food-safety/; Aug. 13, 2019; pp. 1-4.

Payne, Kevin; "Produce Marketing: Brandstorm Offers a Wealth of Insights"; https://www.zestlabs.com/produce-marketing-ideas; Feb. 26, 2019; pp. 1-4.

Payne, Kevin; "Reducing Fresh Food Waste: Addressing the Problem"; https://www.zestlabs.com/reducing-fresh-food-waste-problem/; Mar. 5, 2019; pp. 1-4.

Payne, Kevin; "Rethinking Food Safety and the Supply Chain"; https://www.zestlabs.com/rethinking-food-safety-supply-chain/; May 14, 2019; pp. 1-5.

Payne, Kevin; "Salad Kits: How to Ensure Freshness"; https://www.zestlabs.com/salad-kits-fresh/; Apr. 16, 2019; pp. 1-4.

Payne, Kevin; "Shelf-life Variability at Grocery Stores: Half-bad is Not Good"; https://www.zestlabs.com/shelf-life-variability-among-leading-grocery-stores/; Jun. 10, 2019; pp. 1-4.

Payne, Kevin; "Start the Year Fresh!" https://www.zestlabs.com/start-the-year-fresh/; Jan. 16, 2018; pp. 1-4.

Payne, Kevin; "Supply Chain Waste: Can We Fix the Problem? (Yes)"; https://www.zestlabs.com/supply-chain-waste/; Jul. 30, 2019; pp. 1-5.

Payne, Kevin; "Sustainability and the Supply Chain"; https://www.zestlabs.com/sustainability-supply-chain/; Jun. 18, 2019; pp. 1-4.

Payne, Kevin; "Sustainability or Greenwashing" https://www.zestlabs.com/sustainability-or-greenwashing/; Jan. 23, 2018; pp. 1-4.

Payne, Kevin; "The "Best If Used By" Date Label: Will It Reduce Food Waste?"; https://www.zestlabs.com/best-if-used-by-date-label/; Jun. 4, 2019; pp. 1-4.

Payne, Kevin; "The Emergence of Brand Marketing in Produce"; https://www.zestlabs.com/brand-marketing-produce/; Aug. 20, 2019; pp. 1-4.

Payne, Kevin; "The Grocery Shopping Experience: Fresh Foods, Fresh Ideas"; https://www.zestlabs.com/grocery-shopping-experience-fresh-foods/; May 21, 2019; pp. 1-4.

Payne, Kevin; "To Use or Not to Use—What's Up With Date Labels" https://www.zestlabs.com/date-label/; Jan. 2, 2018; pp. 1-4.

Payne, Kevin; "Want to Improve Your Grocery Margins? Take a Look at Your Supply Chain"; https://www.zestlabs.com/want-to-improve-your-grocery-margins-take-a-look-at-you r-supply-chain/; Dec. 19, 2017; pp. 1-4.

Payne, Kevin; "World Hunger Day 2019: Sustainability"; https://www.zestlabs.com/world-hunger-day-2019-sustainability/; May 28, 2019; pp. 1-4.

Payne, Kevin; "Your Technology Roadmap for Digital Transformation"; https://www.zestlabs.com/technology-roadmap/; Mar. 26, 2019; pp. 1-4.

Payne, Kevin; "A Picture Is Worth . . . "; https://www.zestlabs.com/a-picture-is-worth/; Apr. 3, 2018; pp. 1-4.

Payne, Kevin; "Before and After—The Benefits of Digital Transformation"; https://www.zestlabs.com/benefits-digital-transformation/; Jan. 29, 2019; pp. 1-5.

Payne, Kevin; "Being Proactive: What We Can Learn from Football"; https://www.zestlabs.com/being-proactive-learn-from-football/; Jul. 17, 2018; pp. 1-4.

Payne, Kevin; "Digital Transformation Technology: Is It Finally Time?"; https://www.zestlabs.com/digital-transformation-technology/; Aug. 7, 2018; pp. 1-4.

(56) References Cited

OTHER PUBLICATIONS

Payne, Kevin; "Experience the Many Benefits of Family Meals"; https://www.zestlabs.com/benefits-family-meals/; Sep. 3, 2019; pp. 1-4.
Payne, Kevin; "First Principles Thinking and the Fresh Food Supply Chain"; https://www.zestlabs.com/first-principles-thinking/; Oct. 2, 2018; pp. 1-4.
Payne, Kevin; "Five Days? The Causes of Shelf-life Variability"; https://www.zestlabs.com/five-days-shelf-life-variability/; Nov. 20, 2018; pp. 1-4.
Payne, Kevin; "Food Service Delivery: This Isn't What I Ordered!"; https://www.zestlabs.com/isnt-what-ordered/; Aug. 28, 2018; pp. 1-4.
Payne, Kevin; "Food Spoilage: The Impact on Your Business"; https://www.zestlabs.com/food-spoilage-impact-business/; Jan. 15, 2019; pp. 1-4.
Payne, Kevin; "Food Sustainability Goals: Noble But Are They Viable?"; https://www.zestlabs.com/food-sustainability-goals/; Aug. 14, 2018; pp. 1-4.
Payne, Kevin; "Fresh Food Industry Trends 2019—Our Predictions"; https://www.zestlabs.com/fresh-food-industry-trends-2019/; Jan. 2, 2019; pp. 1-4.
Payne, Kevin; "Fresh Food Industry Trends from 2018"; https://www.zestlabs.com/fresh-food-industry-trends-2018/; Dec. 11, 2018; pp. 1-4.
Payne, Kevin; "Fresh Food Sustainability—It's More Than Field to Fork"; https://www.zestlabs.com/fresh-food-sustainability/; Jan. 22, 2019; pp. 1-4.
Payne, Kevin; "Freshness Capacity: Strawberries Are Like Your Cell Phone . . . "; https://www.zestlabs.com/your-fresh-strawberries-are-like-your-cellphone/; Jul. 10, 2018; pp. 1-4.
Payne, Kevin; "Grocers Are Applying Artificial Intelligence"; https://www.zestlabs.com/grocers-turning-artificial-intelligence/; Oct. 9, 2018; pp. 1-4.
Payne, Kevin; "Growers and Suppliers—What Really Happens in the Food Supply Chain"; https://www.zestlabs.com/what-happens-fresh-food-supply-chain/; Apr. 24, 2018; pp. 1-5.
Payne, Kevin; "Improving Post-Harvest Operational Efficiency"; https://www.zestlabs.com/improving-operational-efficiency/; Sep. 18, 2018; pp. 1-4.
Payne, Kevin; "Is Your Fresh Food Supply Chain Stuck in the '60s?"; https://www.zestlabs.com/is-your-fresh-food-supply-chain-stuck-in-the-60s/; Mar. 13, 2018; pp. 1-4.
Payne, Kevin; "It's (Past) Time for Freshness Management"; https://www.zestlabs.com/managing-fresh-food-shelf-life/; Nov. 27, 2018; pp. 1-4.
Payne, Kevin; "It's Like Waze for the Fresh Food Supply Chain"; https://www.zestlabs.com/waze-fresh-food-supply-chain/; Apr. 10, 2018; pp. 1-5.
Payne, Kevin; "Let's Celebrate National Salad Month!"; https://www.zestlabs.com/lets-celebrate-national-salad-month/; May 1, 2018; pp. 1-4.
Payne, Kevin; "Let's Start at the Beginning"; https://www.zestlabs.com/lets-start-at-the-beginning/; May 15, 2018; pp. 1-4.
Payne, Kevin; "Margins Matter—Don't Get Squeezed"; https://www.zestlabs.com/6931-2/; Apr. 17, 2018; pp. 1-4.
Payne, Kevin; "Perishable Food Waste Cuts Profits & Raises Greenhouse Gases"; https://www.zestlabs.com/food-waste-profits-greenhouse-gases/; Sep. 11, 2018; pp. 1-4.
Payne, Kevin; "PMA Fresh Summit 2018—Wow!"; https://www.zestlabs.com/pma-fresh-summit/; Oct. 23, 2018; pp. 1-4.
Payne, Kevin; "PMA's Fresh Summit: Eat Up!"; https://www.zestlabs.com/pma-fresh-summit-2018/; Oct. 16, 2018; pp. 1-4.
Payne, Kevin; "Poor Quality Produce: Never Going Back Again"; https://www.zestlabs.com/never-going-back-again/; Jul. 3, 2018; pp. 1-4.
Payne, Kevin; "Premature Food Spoilage: Uh Oh, It's the Fuzz!"; https://www.zestlabs.com/uh-oh-its-the-fuzz/; Jun. 19, 2018; pp. 1-4.
Payne, Kevin; "Produce Shelf Life Extenders and Fresh Food Waste"; https://www.zestlabs.com/shelf-life-extenders-food-waste/; Nov. 13, 2018; pp. 1-4.
Payne, Kevin; "Refed: Committed to Reducing U.S. Food Waste"; https://www.zestlabs.com/refed-committed-reducing-waste/; Oct. 30, 2018; pp. 1-4.
Payne, Kevin; "Romaine Lettuce Labeling—Zest Fresh Can Help"; https://www.zestlabs.com/romaine-lettuce-labeling/; Dec. 4, 2018; pp. 1-4.
Payne, Kevin; "Saving Money Day 1—Invest $1, Get $9 Back";https://www.zestlabs.com/saving-money-day-1/; Nov. 6, 2018; pp. 1-4.
Payne, Kevin; "September Is National Family Meals Month"; https://www.zestlabs.com/september-family-meals-month/; Sep. 4, 2018; pp. 1-4.
Payne, Kevin; "Shelf-life Variability in Produce: The Five Causes"; https://www.zestlabs.com/shelf-life-variability-produce-five-causes/; Jan. 8, 2019; pp. 1-4.
Payne, Kevin; "Solving the Problem of Fresh Produce Waste"; https://www.zestlabs.com/solving-problem-fresh-food-waste/; Dec. 18, 2018; pp. 1-4.
Payne, Kevin; "Stay Cool! (And Visit Us at United Fresh!)"; https://www.zestlabs.com/stay-cool-and-visit-us-at-united-fresh/; Jun. 5, 2018; pp. 1-4.
Payne, Kevin; "Stop Doing That!"; https://www.zestlabs.com/stop-doing-that/; May 29, 2018; pp. 1-4.
Payne, Kevin; "Supply Chain Performance: The Fox and the Henhouse"; https://www.zestlabs.com/fox-hen-house/; Jun. 26, 2018; pp. 1-4.
Payne, Kevin; "The Fresh Food Industry and Charles Darwin"; https://www.zestlabs.com/charles-darwin-fresh-food-industry/; Aug. 21, 2018; pp. 1-4.
Payne, Kevin; "The Game of (Shelf) Life"; https://www.zestlabs.com/game-shelf-life/; Sep. 25, 2018; pp. 1-4.
Payne, Kevin; "Timing Is Everything—The Impact of Cut-To-Cool Time on Freshness"; https://www.zestlabs.com/timing-is-everything-the-impact-of-cut-to-cool-time-on- freshness/; May 8, 2018; pp. 1-5.
Payne, Kevin; "What to do to Build Grocery Store Loyalty?"; https://www.zestlabs.com/grocery-store-loyalty/; Jul. 24, 2018; pp. 1-4.
Payne, Kevin; "What? No Bacon? (Cue Ominous Music)"; https://www.zestlabs.com/what-no-bacon-cue-ominous-music/; Mar. 6, 2018; pp. 1-5.
Payne, Kevin; "What's in the Bag?"; https://www.zestlabs.com/whats-in-the-bag/; May 22, 2018; pp. 1-4.
Payne, Kevin; "Where's the Beef (Been)?"; https://www.zestlabs.com/wheres-the-beef-been/; Mar. 27, 2018; pp. 1-5.
Payne, Kevin; "Zest Labs Offers Fresh Wishes for the New Year"; https://www.zestlabs.com/zest-labs-fresh-wishes-new-year/; Dec. 24, 2018; pp. 1-4.
ReFED; "A Roadmap to Reduce U.S. Food Waste by 20 Percent"; https://www.refed.com/downloads/ReFED_Report_2016.pdf; 2016; pp. 1-96.
ReFED; "Restaurant Food Waste Action Guide"; https://www.refed.com/downloads/Restaurant_Guide_Web.pdf; 2018; pp. 1-44.
Ruiz-Garcia, Luis et al.; "Monitoring Cold Chain Logistics by Means of RFID"; http://cdn.intechweb.org/pdfs/8493.pdf; Feb. 1, 2010; pp. 1-16.
Ryan, John; "Why Blockchain Will Be Used to Improve Distribution Food Safety, Quality, and Traceability"; https://www.foodsafetymagazine.com/enewsletter/why-blockchain-will-be-used-to-improve-distribution-food-safety-quality-and-traceability/; Feb. 5, 2019; pp. 1-3.
Scalco, Dan; "5 Ways to Ensure Meals Stay Fresh and Safe in Transit"; https://www.zestlabs.com/meals-stay-fresh-safe-transit/; Jun. 12, 2018; pp. 1-4.
Scotto Di Tella, F.; "Deliverable D8.3.1.1 Newsletter edited by GEIE for industrial use N°1"; http://www.frisbee-project.eu/images/result/FRISBEE_DEL_8.3.1.1.pdf; May 6, 2011; pp. 1-9.
Shacklett, Mary; "Customer Retention and Growth in Today's Competitive Retail Grocery Environment"; https://www.zestlabs.com/downloads/Food-Freshness-and-Customer-Satisfaction-Transworld-Research-April-2019.pdf; Apr. 2019; pp. 1-7.

(56) References Cited

OTHER PUBLICATIONS

Shacklett, Mary; "Improving Profits and Operational Efficiency on the Farm"; https://www.zestlabs.com/downloads/Improving-Operational-Efficiency-on-the-Farm- Transworld-Research-2018.pdf; Available as early as 2018; pp. 1-6.
Shacklett, Mary; "Optimizing Profit Margins in a Changing Retail Grocery Industry"; https://www.zestlabs.com/downloads/Optimizing-Profit-Margins-Transworld.pdf; 2018; pp. 1-10.
Siawsolit, Chokdee et al.; "The Value of Demand Information in Omni-Channel Grocery Retailing"; https://www.researchgate.net/publication/331048136_The_Value_of_Demand_Information_in_Omni-Channel_Grocery_Retailing; Available as early as Jan. 2019; pp. 1-11.
Stahl, Valerie et al.; "Deliverable D.3.2.4.2 Literature review and experimental data of chilled and frozen meat quality and safety models"; http://www.frisbee-project.eu/images/result/FRISBEE_DEL_3.2.4.2.pdf; Jun. 6, 2011; pp. 1-28.
Sunny George, Gwanpua; "Deliverable D3.2.4.1 Literature review and experimental data of chilled apple quality models"; http://www.frisbee-project.eu/images/result/FRISBEE_DEL_3.2.4.1.pdf; Mar. 1, 2011; pp. 1-24.
Swedberg, Claire; "DOD Considers RFID-based Solutions for Tracking Food's Shelf Life"; https://www.rfidjournal.com/articles/pdf?11423; Feb. 11, 2014; pp. 1-3.
Swedberg, Claire; "Researchers Seek to Reduce Wastage for First-Strike Rations"; https://www.rfidjournal.com/articles/pdf?9162; Jan. 26, 2012; pp. 1-4.
Swedberg, Claire; "Schuitema Ponders Future of Fresh-Chain Pilot"; https://www.rfidjournal.com/articles/pdf?3793; Dec. 10, 2007; pp. 1-4.
Swedberg, Claire; "Starbucks Keeps Fresh with RFID"; https://www.rfidjournal.com/articles/view?2890; Dec. 13, 2006; pp. 1-1.
Taoukis, P. S., et al.; "Applicability of Time-Temperature Indicators as Shelf Life Monitors of Food Products"; Journal of Food Science; vol. 54, Issue 4; Jul. 1989; pp. 783-788.
Taoukis, P. S., et al.; "Use of time-temperature integrators and predictive modelling for shelf life control of chilled fish under dynamic storage conditions"; International Journal of Food Microbiology, vol. 53; 1999; pp. 21-31.
Taoukis, Petros et al.; "Deliverable D.2.1.2 Temperature monitoring techniques and traceability systems along the cold chain";http://www.frisbee-project.eu/images/result/FRISBEE_DEL_2%201%202.pdf; Jul. 26, 2011; pp. 1-28.
Taoukis, Petros; "Deliverable D 3.2.4.4 Literature review and experimental data of frozen milk products and vegetables quality models"; http://www.frisbee-project.eu/images/result/FRISBEE_DEL_3-2-4-4.pdf; Jun. 6, 2011; pp. 1-24.
This New World by Huffpost; "Eating Ugly: The Food Waste That Could Refeed America"; https://www.facebook.com/ThisNewWorldHuffPost/videos/428476821288487; Apr. 22, 2019; pp. 1-9.
Trust in Food™; "Sustainability Research Report 2019"; https://www.zestlabs.com/downloads/Trust-In-Food-Sustainability-Survey-2019.pdf; Available as early as Jul. 18, 2019; pp. 1-19.
United States Army Medical Command; "U.S. Army Veterinary Command Guidelines and Procedures"; https://www.dla.mil/Portals/104/Documents/TroopSupport/Subsistence/Rations/qapubs/medcom/40-13.pdf; Feb. 13, 2006; pp. 1-171.
Wells, John H., et al.; "A Kinetic Approach to Food Quality Prediction using Full-History Time-Temperature Indicators"; Journal of Food Science; vol. 53, Issue 6; Nov. 1988; pp. 1866-1871.
Wells, John H., et al.; "A Quality-Based Inventory Issue Policy for Perishable Foods"; Journal of Food Processing & Preservation; vol. 12, Issue 4; Jan. 1989; pp. 271-292.
Wells, John Henry, et al.; "Application of Time-Temperature Indicators in Monitoring Changes in Quality Attributes of Perishable and Semiperishable Foods"; Journal of Food Science; vol. 53, Issue 1; Jan. 1988; pp. 148-152, 156.
Weston, L.A. et. al.; "Preharvest Factors Affecting Postharvest Quality of Vegetables"; HortScience; vol. 32(5), Aug. 1997, pp. 812-816.
Williamson, Katie et al.; "Climate Change Needs Behavior Change"; https://www.zestlabs.com/downloads/2018-CCNBC-Report.pdf; 2018; pp. 1-22.
Zelem, MC.; "Deliverable D.2.3.1 National legal and ethical requirements for the surveys"; http://www.frisbee-project.eu/images/result/FRISBEE_DEL_2.3.1.pdf; Jun. 23, 2011; pp. 1-68.
*Zest Labs, Inc.* v *Walmart*; Bohling, Joshua; "Transcript of the Testimony of Bohling, Joshua"; Bushman Court Reporting; Case No. 4:18-CV-00500-JM; Aug. 15-16, 2019; pp. 5-6, 47-48, 52-69, 78, 80-82, 85, 87, 98-102, 107-134, 137-145, 158-163, 182-184, 209-210, 233-234, 239-242, 246, and 357.
*Zest Labs, Inc.* v *Walmart*; Dickinson, Q. Todd; "Expert Report of Q. Todd Dickinson"; United States District Court for the Eastern District of Arkansas; Case No. 4:18-CV-00500-JM; Oct. 29, 2019; pp. 1-33.
*Zest Labs, Inc.* v *Walmart*; Kunin, Stephen G.; "Rebuttal Expert Report of Stephen G. Kunin"; United States District Court for the Eastern District of Arkansas; Case No. 4:18-CV-00500-JM; Nov. 25, 2019; pp. 1-38.
*Zest Labs, Inc.* v *Walmart*; Zest Labs, Inc. et al.; "Complaint"; United States District Court for the Eastern District of Arkansas; Case No. 4:18-CV-00500-JM; Aug. 1, 2018; pp. 1-26.
Zest Labs; "Blockchain for Supply Chains"; https://www.zestlabs.com/challenges/blockchain-for-supply-chains/; Available as early as Jul. 18, 2019; pp. 1-4.
Zest Labs; "Food Safety and the Supply Chain"; https://www.zestlabs.com/challenges/food-safety/; Available as early as Jul. 18, 2019; pp. 1-5.
Zest Labs; "Food Supplier Operational Efficiency"; https://www.zestlabs.com/challenges/food-supplier-operational-efficiency/; Available as early as Jul. 18, 2019; pp. 1-5.
Zest Labs; "Food Waste is a Significant Problem"; https://www.zestlabs.com/challenges/food-waste-challenge/; Available as early as Jul. 18, 2019; pp. 1-6.
Zest Labs; "Fresh Food Supply Chain"; https://www.zestlabs.com/challenges/fresh-food-supply-chain/; Available as early as Jul. 18, 2019; pp. 1-5.
Zest Labs; "Fresh Food Sustainability"; https://www.zestlabs.com/challenges/fresh-food-sustainability/; Available as early as Jul. 18, 2019; pp. 1-4.
Zest Labs; "Fresh Produce"; http://www.zestlabs.com/fresh-produce; Available as early as Oct. 21, 2017; pp. 1-14.
Zest Labs; "On-Demand Delivery"; https://www.zestlabs.com/on-demand-delivery/; Available as early as Oct. 22, 2017; pp. 1-7.
Zest Labs; "Post-Harvest Technology"; https://www.zestlabs.com/challenges/post-harvest-technology/; Available as early as Jul. 18, 2019; pp. 1-8.
Zest Labs; "The Freshest Produce"; https://www.zestlabs.com/resources; Available as early as May 2, 2018; pp. 1-16.
Zest Labs; "Zest Fresh—Deep Dive"; https://www.zestlabs.com/resources; Available as early as May 2, 2018; pp. 1-15.
Zest Labs; "Zest Fresh Differentiation"; https://www.zestlabs.com/zest-fresh-differentiation/; Available as early as Jul. 18, 2019; pp. 1-6.
Zest Labs; "Zest Fresh for Beef, Poultry, Pork and Seafood"; https://www.zestlabs.com/zest-fresh-for-protein/; Available as early as Jul. 18, 2019; pp. 1-5.
Zest Labs; "Zest Fresh for Grocers"; https://www.zestlabs.com/zest-fresh-for-produce-for-grocers/; Available as early as Jul. 18, 2019; pp. 1-13.
Zest Labs; "Zest Fresh for Growers, Packers, and Shippers"; https://www.zestlabs.com/zest-fresh-for-growers-and-suppliers/; Available as early as Jul. 18, 2019; pp. 1-17.
Zest Labs; "Zest Fresh for Restaurants"; https://www.zestlabs.com/zest-fresh-for-produce-for-restaurants/; Available as early as Jul. 18, 2019; pp. 1-13.
Zest Labs; "Zest Fresh Grower Testimonial"; https://www.zestlabs.com/resources; Available as early as May 2, 2018; pp. 1-13.
Zest Labs; "Zest Fresh Overview"; https://www.zestlabs.com/resources; Available as early as May 2, 2018; pp. 1-19.
Zest Labs; "Zest Fresh Use Cases"; https://www.zestlabs.com/zest-fresh-use-cases/; Available as early as Jul. 18, 2019; pp. 1-6.

(56) References Cited

OTHER PUBLICATIONS

Zest Labs; "Zest Fresh: Pallet-level Quality Management from Harvest to Store"; http://www.zestlabs.com/zest-fresh; Available as early as Oct. 29, 2017; pp. 1-10.
Zest Labs; "Zest Labs Overview"; https://www.zestlabs.com/resources; Available as early as Aug. 1, 2018; pp. 1-13.
Zest Labs; ". . . Not Worth a Thousand Words—Why Traditional Temperature Loggers and Imaging Technologies are Inadequate to Determine Freshness and Reduce Waste"; https://www.zestlabs.com/wp-content/uploads/2018/03/WP-05-0318-Not-Worth-A-Thous and-Words.pdf; Mar. 5, 2018; pp. 1-6.
Zest Labs; "10 Limitations of Traditional Temperature Data Loggers and Why They're No Longer Adequate for the Cold Chain"; https://www.zestlabs.com/wp-content/uploads/2018/05/PB-04-0418-10-Limitations-of -Data-Loggers.pdf; May 4, 2018; pp. 1-3.
Zest Labs; "Before and After—The Benefits of Digital Transformation in the Fresh Food Supply Chain"; https://www.zestlabs.com/downloads/Before-and-After-Digital-Transformation.pdf; Jan. 13, 2019; pp. 1-6.
Zest Labs; "Blockchain and Achieving True Transparency—Proactively Managing Food Safety and Freshness with Blockchain and IoT Technologies"; https://www.zestlabs.com/wp-content/uploads/2018/01/WP-08-0118.Blockchain.and_.Achieving.True_.Transparency-1.pdf; Jan. 8, 2018; pp. 1-4.
Zest Labs; "Blockchain and Its Value to Suppliers"; https://www.zestlabs.com/downloads/Blockchain-and-Its-Value-to-Suppliers.pdf; Available as early as Jul. 18, 2019; pp. 1-5.
Zest Labs; "Comparing Pallet- and Trailer-level Temperature Monitoring—Implications on Quality, Freshness, Traceability and Profitability for Retail Grocers"; https://www.zestlabs.com/wp-content/uploads/2018/03/WP-04-0318-Pallet-vs-Trailer .pdf; Mar. 4, 2018; pp. 1-4.
Zest Labs; "Freshness Baseline Study—Sample Report"; http://www.zestlabs.com/wp-content/uploads/2018/03/Zest-Labs-Sample-Baseline-Rep ort.pdf; Available as early as Mar. 2018; pp. 1-11.
Zest Labs; "Freshness Myths—False Beliefs That Lead to Food Waste"; https://www.zestlabs.com/downloads/Freshness-Myths.pdf; Aug. 7, 2018; pp. 1-5.
Zest Labs; "Half-bad Is Not Good"; https://www.zestlabs.com/downloads/Grocery-Store-Variability.pdf; Jun. 15, 2019; pp. 1-11.
Zest Labs; "Improve Operational Efficiency—Optimize Labor and Process Adherence to Reduce Costs"; https://www.zestlabs.com/downloads/Improving-Operational-Efficiency.pdf; Available as early as Jul. 18, 2019; pp. 1-3.
Zest Labs; "Improving Quality and Profitability for Retail Grocers—The Benefits of Pallet-level Monitoring for the Fresh and Perishable Food Cold Chain"; https://www.zestlabs.com/wp-content/uploads/2017/12/WP-01-1117.Improving.Quality .and_.Profitability.for_.Retail.Grocers.pdf; Nov. 1, 2017; pp. 1-8.
Zest Labs; "Let's Start at the Beginning—Reducing Shrink Begins at Harvest"; https://www.zestlabs.com/wp-content/uploads/2018/05/WP-12-0518-Lets-Start-at-the -Beginning.pdf; May 12, 2018; pp. 1-4.
Zest Labs; "Margins Matter—Reducing Fresh Food Waste to Improve Product Margins by 6% or More"; https://www.zestlabs.com/wp-content/uploads/2018/04/WP-11-0418-Margins-Matter-1. pdf; Apr. 11, 2018; pp. 1-6.
Zest Labs; "Measuring and Managing Operational Efficiency for Growers and Suppliers"; https://www.zestlabs.com/downloads/Zest-Fresh-Metrics-Datasheet.pdf; Aug. 25, 2019; pp. 1-5.
Zest Labs; "Monitoring the Safety and Quality of Fresh, Frozen and Processed Foods"; https://www.zestlabs.com/wp-content/uploads/2016/03/IN-SB-FreshProduce_RestaurantFoodService_031016.pdf; Mar. 10, 2016; pp. 1-2.
Zest Labs; "Pallet-level Quality Management from Harvest to Store"; https://www.zestlabs.com/wp-content/uploads/2016/03/IN_SB_FoodIndustry_ProduceGr owers_031016.pdf; Mar. 10, 2016; pp. 1-2.
Zest Labs; "Poor Customer Experiences—Half-Bad is Not Good! A Shelf-Life Variability Study"; https://www.zestlabs.com/downloads/Variability-Infographic.pdf; Available as early as Jul. 2019; pp. 1-1.
Zest Labs; "Proactive Freshness Management: Modernizing the Fresh Food Supply Chain to Reduce Waste and Improve Profitability"; https://www.zestlabs.com/downloads/Proactive-Freshness-Management.pdf; Feb. 6, 2019; pp. 1-7.
Zest Labs; "Reduce Shrink, Improve Profitability and Quality for Fresh Food"; https://www.zestlabs.com/wp-content/uploads/2016/03/IN-SB-FreshProduce_RetailGro cers_031016.pdf; Mar. 10, 2016; pp. 1-3.
Zest Labs; "Shelf-life Variability Begins in the Field—Produce Pallets Harvested on the Same Day Vary by as Much as 86 Percent, Contributing to Shrink and Lost Profits"; https://www.zestlabs.com/wp-content/uploads/2018/02/WP-10-0218-Shelf-life-Variab ility.pdf; Feb. 10, 2018; pp. 1-4.
Zest Labs; "Strawberries—Shelf-Life Variability"; https://www.zestlabs.com/downloads/Zest-Fresh-Strawberries-Report.pdf; Available as early as Jul. 2019; pp. 1-2.
Zest Labs; "The Best of Zest 2018—A Collection of Our Most Popular Blogs"; https://www.zestlabs.com/downloads/The-Best-of-Zest-2018.pdf; Available as early as 2018; pp. 1-15.
Zest Labs; "The ZIPR Code Freshness Metric—Dynamically providing the current freshness of each pallet to help you intelligently manage product and reduce shrink throughout the fresh food supply chain"; https://www.zestlabs.com/downloads/The-ZIPR-Code.pdf; Jun. 1, 2018; pp. 1-3.
Zest Labs; "Today, You Saved $67,571—How Zest Fresh for Managing the Produce Cold Chain Reduces Waste and Saves Retailers Money . . . Beginning on Day One"; https://www.zestlabs.com/downloads/Today-You-Saved.pdf; Jun. 3, 2018; pp. 1-6.
Zest Labs; "True Transparency for Freshness Management, Food Safety, Authenticity and Traceability"; https://www.zestlabs.com/wp-content/uploads/2018/03/SO-04-0218-Zest-Fresh-for-Protein-Solution-Overview.pdf; Feb. 4, 2018; pp. 1-2.
Zest Labs; "Zest Labs FAQ and Reference Guide"; https://www.zestlabs.com/downloads/Zest-Labs-FAQ-and-Reference-Guide.pdf; Jul. 1, 2018; pp. 1-6.
Zest Labs; "Zest Labs Professional Services"; https://www.zestlabs.com/wp-content/uploads/2018/03/SO-05-0318-Zest-Labs-Profess ional-Services.pdf; Mar. 5, 2018; pp. 1-2.
Haard, Norman F., et al.; "Characteristics of Edible Plant Tissues"; Food Chemistry, edited by Owen R. Fennema; 3rd Ed.; Marcel Dekker, Inc.; 1996; pp. 943-1011.
Haugen, John E., et al.; "Application of gas-sensor array technology for detection and monitoring of growth of spoilage bacteria in milk: A model study"; Analytica Chimica Acta; vol. 565, No. 1; https://doi.org/10.1016/j.aca.2006.02.016; Feb. 23, 2006; pp. 10-16.
Kader, Adel A., et al.; "Technologies to Extend the Refrigerated Shelf Life of Fresh Fruit"; Food Storage Stability, edited by Irwin A. Taub, et al.; Boca Raton; CRC Press; 1998; pp. 1-27.
Kader, Adel A.; "Postharvest Technology of Horticultural Crops"; 2002; 3rd Ed.; University of California Agriculture and Natural Resources; Oakland; 56 pages.
Kader, Adel A.; "Postharvest Technology of Horticultural Crops"; 2002; 3rd Ed.; University of California Agriculture and Natural Resources; Oakland; 74 pages.
Kader, Adel A.; "Postharvest Technology of Horticultural Crops"; 2002; 3rd Ed.; University of California Agriculture and Natural Resources; Oakland; pp. 113-196.
Kader, Adel A.; "Postharvest Technology of Horticultural Crops"; 2002; 3rd Ed.; University of California Agriculture and Natural Resources; Oakland; pp. 197-250.
Kader, Adel A.; "Postharvest Technology of Horticultural Crops"; 2002; 3rd Ed.; University of California Agriculture and Natural Resources; Oakland; pp. 251-314.
Kader, Adel A.; "Postharvest Technology of Horticultural Crops"; 2002; 3rd Ed.; University of California Agriculture and Natural Resources; Oakland; pp. 315-384.
Kader, Adel A.; "Postharvest Technology of Horticultural Crops"; 2002; 3rd Ed.; University of California Agriculture and Natural Resources; Oakland; pp. 385-434.

(56) References Cited

OTHER PUBLICATIONS

Kader, Adel A.; "Postharvest Technology of Horticultural Crops"; 2002; 3rd Ed.; University of California Agriculture and Natural Resources; Oakland; pp. 435-480.
Kader, Adel A.; "Postharvest Technology of Horticultural Crops"; 2002; 3rd Ed.; University of California Agriculture and Natural Resources; Oakland; pp. 67-112.
Kong, F. et al.; "Chemical Deterioration and Physical Instability of Foods and Beverages"; The Stability and Shelf Life of Food, edited by Persis Subramaniam; 2nd Ed.; Woodhead Publishing; 2016; pp. 1-21.
Labuza, T. P., et al.; "The Relationship Between Processing and Shelf Life"; Foods forthe '90s, edited by Gordon G. Birch, et al.; Elsevier Applied Science; Aug. 1, 1990; pp. 1-21.
National Geographic Society, Season, Sep. 22, 2016 (Year: 2016).
Robertson, Gordon L.; "Food Packaging: Principles and Practice"; 3rd Ed.; Boca Raton; CRC Press; 2013; pp. 1-33.
Singh, R. P.; "Scientific Principles of Shelf-Life Evaluation"; Shelf-Life Evaluation of Foods, edited by Dominic Man, et al.; 2nd Ed.; Aspen Publishers, Inc.; 2000; pp. 1-23.
Singh, R. Paul et al.; "Introduction to Food Engineering"; 5th Ed.; Academic Press; 2014; pp. 1-31.
Wells, John H. et al.; "Quality Management During Storage and Distribution"; Food Storage Stability, edited by Irwin A. Taub, et al.; Boca Raton; CRC Press; 1998; pp. 1-29.
Wells, John H., et al.; "Temperature Tolerance of Foods during Distribution"; Handbook of Food Engineering Practice, edited by Kenneth J. Valentas, et al.; Boca Raton; CRC Press; 1997; pp. 1-29.
Wells, John H., et al.; "The Application of Time-Temperature Indicator Technology to Food Quality Monitoring and Perishable Inventory Management"; Mathematical Modelling of Food Processing Operations, edited by Stuart Thorne; Elsevier Applied Science; 1992; pp. 1-41.
Zest Labs, Inc. v Walmart; ECF No. 002; Zest Labs, Inc. et al.; "Motion for Leave To File Complaint Under Sealand To Establish Briefing Schedule Relating To Potentially Confidential Information in Complaint"; United States District Court for the Eastern District of Arkansas; Case No. 4:18-CV-00500-JM; Aug. 1, 2018; pp. 1-4.
Zest Labs, Inc. v Walmart; ECF No. 003; Zest Labs, Inc. et al.; "Brief in Support of Motion for Leave To File Complaint Under Sealand To Establish Briefing Schedule Relating To Potentially Confidential Information Complaint"; United States District Court for the Eastern District of Arkansas; Case No. 4:18-CV-00500-JM; Aug. 1, 2018; pp. 1-4.
Zest Labs, Inc. v Walmart; ECF No. 035; Walmart; "Defendant's Response To Plaintiffs' Motion for Leave To File Complaint Under Seal"; United States District Court for the Eastern District of Arkansas; Case No. 4:18-CV-00500-JM; Aug. 27, 2018; pp. 1-3.
Zest Labs, Inc. v Walmart; ECF No. 038; Zest Labs, Inc. et al.; "Plaintiffs' Reply in Support of Plaintiffs' Motion for Leave To File Complaint Under Seal"; United States District Court for the Eastern District of Arkansas; Case No. 4:18-CV-00500-JM; Aug. 31, 2018; pp. 1-3.
Zest Labs, Inc. v Walmart; ECF No. 041; Walmart; "Defendant's Motion for Leave To File Under Seal"; United States District Court for the Eastern District of Arkansas; Case No. 4:18-CV-00500-JM; Sep. 4, 2018; pp. 1-3.
Zest Labs, Inc. v Walmart; ECF No. 098; Walmart; "Defendant's Brief in Support of Its Motion for Protective Order and To Compel Identification of Alleged Trade Secrets"; United States District Court for the Eastern District of Arkansas; Case No. 4:18-CV-00500-JM; Feb. 11, 2019; pp. 1-29.
Zest Labs, Inc. v Walmart; ECF No. 101-01; Sammi, P. Anthony; "Exhibit A"; United States District Court for the Eastern District of Arkansas; Case No. 4:18-CV-00500-JM; Feb. 15, 2019; pp. 1-3.
Zest Labs, Inc. v Walmart; ECF No. 101-02; Tulin, Edward L.; "Exhibit B"; United States District Court for the Eastern District of Arkansas; Case No. 4:18-CV-00500-JM; Feb. 15, 2019; pp. 1-4.
Zest Labs, Inc. v Walmart; ECF No. 101-03; Tulin, Edward L.;" Exhibit C"; United States District Court for the Eastern District of Arkansas; Case No. 4:18-CV-00500-JM; Feb. 15, 2019; pp. 1-5.
Zest Labs, Inc. v Walmart; ECF No. 101 -04; Zest Labs, Inc et al.; "Exhibit D Filed Under Seal Pursuant To Order Dated Sep. 7, 2018"; United States District Court for the Eastern District of Arkansas; Case No. 4:18-CV-00500-JM; Feb. 15, 2019; 1 page.
Zest Labs, Inc. v Walmart; ECF No. 101-05; Zest Labs, Inc. et al.; "Exhibit E Filed Under Seal Pursuant To Order Dated Sep. 7, 2018"; United States District Court for the Eastern District of Arkansas; Case No. 4:18-CV-00500-JM; Feb. 15, 2019; 1 page.
Zest Labs, Inc. v Walmart; ECF No. 101; Zest Labs, Inc. et al.; "Plaintiffs' Brief in Opposition To Defendant's Motion for Protective Order and To Compel Identification of Trade Secrets"; United States District Court for the Eastern District of Arkansas; Case No. 4:18-CV-00500-JM; Feb. 15, 2019; pp. 1-28.
Zest Labs, Inc. v Walmart; ECF No. 102-01; Zest Labs, Inc. et al.; "Exhibit A"; United States District Court for the Eastern District of Arkansas; Case No. 4:18-CV-00500-JM; Feb. 20, 2019; pp. 1-28.
Zest Labs, Inc. v Walmart; ECF No. 102-02; Walmart; "Exhibit B"; United States District Court for the Eastern District of Arkansas; Case No. 4:18-CV-00500-JM; Feb. 20, 2019; pp. 1-59.
Zest Labs, Inc. v Walmart; ECF No. 102-03; Zest Labs, Inc. et al.; "Exhibit C Filed Under Seal"; United States District Court for the Eastern District of Arkansas; Case No. 4:18-CV-00500-JM; Feb. 20, 2019; 1 page.
Zest Labs, Inc. v Walmart; ECF No. 102-04; Walmart; "Exhibit D"; United States District Court for the Eastern District of Arkansas; Case No. 4:18-CV-00500-JM; Feb. 20, 2019; pp. 1-10.
Zest Labs, Inc. v Walmart; ECF No. 102-06; Zest Labs, Inc. et al.; "Exhibit F Filed Under Seal"; United States District Court for the Eastern District of Arkansas; Case No. 4:18-CV-00500-JM; Feb. 20, 2019; 1 page.
Zest Labs, Inc. v Walmart; ECF No. 102-07; Zest Labs, Inc. et al.; "Exhibit G Filed Under Seal"; United States District Court for the Eastern District of Arkansas; Case No. 4:18-CV-00500-JM; Feb. 20, 2019; 1 page.
Zest Labs, Inc. v Walmart; ECF No. 102-08; Williams, Fred I.; "Exhibit H"; United States District Court for the Eastern District of Arkansas; Case No. 4:18-CV-00500-JM; Feb. 20, 2019; pp. 1-5.
Zest Labs, Inc. v Walmart; ECF No. 102-09; Simons, Michael; "Exhibit I"; United States District Court for the Eastern District of Arkansas; Case No. 4:18-CV-00500-JM; Feb. 20, 2019; pp. 1-8.
Zest Labs, Inc. v Walmart; ECF No. 102-10; Williams, Fred I.; "Exhibit J"; United States District Court for the Eastern District of Arkansas; Case No. 4:18-CV-00500-JM; Feb. 20, 2019; pp. 1-4.
Zest Labs, Inc. v Walmart; ECF No. 102-11; Simons, Michael; "Exhibit K"; United States District Court for the Eastern District of Arkansas; Case No. 4:18-CV-00500-JM; Feb. 20, 2019; pp. 1-2.
Zest Labs, Inc. v Walmart; ECF No. 102-12; Tulin, Edward L.; "Exhibit L"; United States District Court for the Eastern District of Arkansas; Case No. 4:18-CV-00500-JM; Feb. 20, 2019; pp. 1-4.
Zest Labs, Inc. v Walmart; ECF No. 102-13; Sammi, P. Anthony; "Exhibit M"; United States District Court for the Eastern District of Arkansas; Case No. 4:18-CV-00500-JM; Feb. 20, 2019; pp. 1-3.
Zest Labs, Inc. v Walmart; ECF No. 102-14; Sammi, P. Anthony; "Exhibit N"; United States District Court for the Eastern District of Arkansas; Case No. 4:18-CV-00500-JM; Feb. 20, 2019; pp. 1-3.
Zest Labs, Inc. v Walmart; ECF No. 102; Zest Labs, Inc. et al.; "Plaintiffs' Motion To Compel Supplemental Responses To Interrogatories and Requests for Production From Defendant"; United States District Court for the Eastern District of Arkansas; Case No. 4:18-CV-00500-JM; Feb. 20, 2019; pp. 1-6.
Zest Labs, Inc. v Walmart; ECF No. 103; Zest Labs, Inc. et al.; "Plaintiffs' Brief in Support of Motion To Compel Supplemental Responses To Interrogatories and Requests for Production From Defendant"; United States District Court for the Eastern District of Arkansas; Case No. 4:18-CV-00500-JM; Feb. 20, 2019; pp. 1-24.
Zest Labs, Inc. v Walmart; ECF No. 105-1; Walmart; "Exhibit A—Filed Under Seal Pursuant To Order Dated Sep. 7, 2018"; United States District Court for the Eastern District of Arkansas; Case No. 4:18-CV-00500-JM; Feb. 25, 2019; 1 page.

(56) References Cited

OTHER PUBLICATIONS

*Zest Labs, Inc.* v *Walmart*; ECF No. 105; Walmart; "Defendant's Response To Plaintiffs' Motion To Compel"; United States District Court for the Eastern District of Arkansas; Case No. 4:18-CV-00500-JM; Feb. 25, 2019; pp. 1-21.

*Zest Labs, Inc.* v *Walmart*; ECF No. 125; Zest Labs, Inc. et al.; "Plaintiffs' Motion To Compel Defendant Walmart To Comply With the Court's Mar. 6, 2019 Order and Otherwise Produce Technical Discovery"; United States District Court for the Eastern District of Arkansas; Case No. 4:18-CV-00500-JM; Apr. 22, 2019; pp. 1-9.

*Zest Labs, Inc.* v *Walmart*; ECF No. 126; Zest Labs, Inc. et al.; "Plaintiffs' Brief in Support of Motion To Compel Defendant Walmart To Comply With the Court's Mar. 6, 2019 Order and Otherwise Produce Technical Discovery"; United States District Court for the Eastern District of Arkansas; Case No. 4:18-CV-00500-JM; Apr. 22, 2019; pp. 1-21.

*Zest Labs, Inc.* v *Walmart*; ECF No. 130-1; Sammi, P. Anthony; "*Zest V. Walmart*: Mar. 29, 2019 M. Simons Letter To P. Sammi Re Deficient Production of Technical Documents"; United States District Court for the Eastern District of Arkansas; Case No. 4:18-CV-00500-JM; May 8, 2019; pp. 1-2.

*Zest Labs, Inc.* v *Walmart*; ECF No. 130-2; Tulin, Edward L.; "*Zest v. Walmart*: Deposition Notices"; United States District Court for the Eastern District of Arkansas; Case No. 4:18-CV-00500-JM; May 8, 2019; pp. 1-2.

*Zest Labs, Inc.* v *Walmart*; ECF No. 130-3; Simons, Michael; "*Zest v. Walmart*: Deposition Notices"; United States District Court for the Eastern District of Arkansas; Case No. 4:18-CV-00500-JM; May 8, 2019; pp. 1-3.

*Zest Labs, Inc.* v *Walmart*; ECF No. 130-4; Walmart; "Exhibit D—Filed Under Seal Pursuant To Order Dated Sep. 7, 2018"; United States District Court for the Eastern District of Arkansas; Case No. 4:18-CV-00500-JM; May 8, 2019; 1 page.

*Zest Labs, Inc.* v *Walmart*; ECF No. 130-5; Simons, Michael; "*Zest Labs v. Walmart*—Walmart's Apr. 5, 2019 Production"; United States District Court for the Eastern District of Arkansas; Case No. 4:18-CV-00500-JM; May 8, 2019; pp. 1-2.

*Zest Labs, Inc.* v *Walmart*; ECF No. 130; Walmart; "Defendant'S Response To Plaintiffs' Motion To Compel Compliance With the Mar. 6, 2019 Order and Technical Discovery"; United States District Court for the Eastern District of Arkansas; Case No. 4:18-CV-00500-JM; May 8, 2019; pp. 1-26.

*Zest Labs, Inc.* v *Walmart*; ECF No. 131-1; Walmart; "Exhibit A—Filed Under Seal Pursuant To Order Dated Sep. 7, 2018"; United States District Court for the Eastern District of Arkansas; Case No. 4:18-CV-00500-JM; May 8, 2019; 1 page.

*Zest Labs, Inc.* v *Walmart*; ECF No. 131-2; Walmart; "Exhibit B—Filed Under Seal Pursuant To Order Dated Sep. 7, 2018"; United States District Court for the Eastern District of Arkansas; Case No. 4:18-CV-00500-JM; May 8, 2019; 1 page.

*Zest Labs, Inc.* v *Walmart*; ECF No. 131-3; Sammi, P. Anthony; "Re: 4:18-CV-00500-JM *Zest Labs Inc. et al v. Wal-Mart Inc*"; United States District Court for the Eastern District of Arkansas; Case No. 4:18-CV-00500-JM; May 8, 2019; 1 page.

*Zest Labs, Inc.* v *Walmart*; ECF No. 131-4; Simons, Michael; "Re: 4:18-CV-00500-JM *Zest Labs Inc. et al v. Wal-Mart Inc*"; United States District Court for the Eastern District of Arkansas; Case No. 4:18-CV-00500-JM; May 8, 2019; 1 page.

*Zest Labs, Inc.* v *Walmart*; ECF No. 131; Walmart; "Defendant's Sur-Reply Brief in Further Opposition To Plaintiffs' Motion To Compel"; United States District Court for the Eastern District of Arkansas; Case No. 4:18-CV-00500-JM; May 8, 2019; pp. 1-21.

*Zest Labs, Inc.* v *Walmart*; ECF No. 250; Walmart; "Defendant's Reply Brief in Support of Its Motion To Exclude Proposed Expert Testimony of Patent Attorney Q. Todd Dickinson"; United States District Court for the Eastern District of Arkansas; Case No. 4:18-CV-00500-JM; Mar. 27, 2020; pp. 1-13.

*Zest Labs, Inc.* v *Walmart*; ECF No. 257-1; Walmart; "Defendant's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 1-168.

*Zest Labs, Inc.* v *Walmart*; ECF No. 257-1; Walmart; "Defendant's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 169-336.

*Zest Labs, Inc.* v *Walmart*; ECF No. 257-1; Walmart; "Defendant's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 337-342.

*Zest Labs, Inc.* v *Walmart*; ECF No. 257; Walmart; "Defendant's Motion for Leave To File Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 1-3.

*Zest Labs, Inc.* v *Walmart*; ECF No. 261-1; Blitzer, Rachel R.; "Declaration of Rachel R. Blitzer Regarding Walmart's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 1-169.

*Zest Labs, Inc.* v *Walmart*; ECF No. 261-1; Blitzer, Rachel R.; "Declaration of Rachel R. Blitzer Regarding Walmart's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 170-337.

*Zest Labs, Inc.* v *Walmart*; ECF No. 261; Walmart; "Defendant's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 1-5.

*Zest Labs, Inc.* v *Walmart*; ECF No. 262; Walmart; "Brief in Support of Defendant's Motion for Summary Judgment"; United States District Court for the Eastern District of Arkansas; Case No. 4:18-CV-00500-JM; Apr. 21, 2020; pp. 1-54.

*Zest Labs, Inc.* v *Walmart*; ECF No. 263; Walmart; "Defendant's Motion To Exclude Certain Proposed Expert Testimony of Mark Lanning"; United States District Court for the Eastern District of Arkansas; Case No. 4:18-CV-00500-JM; Apr. 21, 2020; pp. 1-6.

*Zest Labs, Inc.* v *Walmart*; ECF No. 264; Walmart; "Brief in Support of Defendant's Motion To Exclude Proposed Expert Testimony of Mark Lanning"; United States District Court for the Eastern District of Arkansas; Case No. 4:18-CV-00500-JM; Apr. 21, 2020; pp. 1-26.

*Zest Labs, Inc.* v *Walmart*; ECF No. 265; Walmart; "Defendant's Motion To Exclude Testimony of Damages Expert Stephen L. Becker, Ph.D."; United States District Court for the Eastern District of Arkansas; Case No. 4:18-CV-00500-JM; Apr. 21, 2020; pp. 1-7.

*Zest Labs, Inc.* v *Walmart*; ECF No. 266; Walmart; "Brief in Support of Defendant's Motion To Exclude Testimony of Damages Expert Stephen L. Becker, Ph.D."; United States District Court for the Eastern District of Arkansas; Case No. 4:18-CV-00500-JM; Apr. 21, 2020; pp. 1-22.

*Zest Labs, Inc.* v *Walmart*; ECF No. 267; Walmart; "Defendant's Response To Zest Labs, Inc.'s Motion for Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-23.

*Zest Labs, Inc.* v *Walmart*; ECF No. 268; Walmart; "Defendant's Response To Zest Labs, Inc.'s Motion for Partial Summary Judgment That Walmart Used and Disclosed Zest Labs' Information in

(56) References Cited

OTHER PUBLICATIONS the Walmart Applications"; United States District Court for the Eastern District of Arkansas; Case No. 4:18-CV-00500-JM; Apr. 21, 2020; pp. 1-29.

*Zest Labs, Inc. v Walmart*; ECF No. 269; Walmart; "Defendant's Response To Plaintiffs' Motion To Exclude Testimony of Walmart's Damages Expert, Dr. William Choi"; United States District Court for the Eastern District of Arkansas; Case No. 4:18-CV-00500-JM; Apr. 21, 2020; pp. 1-17.

*Zest Labs, Inc. v Walmart*; ECF No. 270; Walmart; "Defendant's Response To Plaintiffs' Motion To Exclude Testimony of Walmart's Technical Expert, Dr. David Dobkin, Ph.D."; United States District Court for the Eastern District of Arkansas; Case No. 4:18-CV-00500-JM; Apr. 21, 2020; pp. 1-13.

*Zest Labs, Inc. v Walmart*; ECF No. 271; Walmart; "Defendant's Response To Plaintiffs' Motion To Exclude Testimony of Walmart's Technical Expert, Dr. Catherine Adams Hutt, Ph.D."; United States District Court for the Eastern District of Arkansas; Case No. 4:18-CV-00500-JM; Apr. 21, 2020; pp. 1-25.

*Zest Labs, Inc. v Walmart*; ECF No. 272; Walmart; "Defendant's Reply Brief in Support of Its Motion To Exclude Testimony of Damages Expert Stephen L. Becker, Ph.D."; United States District Court for the Eastern District of Arkansas; Case No. 4:18-CV-00500-JM; Apr. 21, 2020; pp. 1-22.

*Zest Labs, Inc. v Walmart*; ECF No. 273; Walmart; "Defendant's Reply Brief in Support of Its Motion for Summary Judgment"; United States District Court for the Eastern District of Arkansas; Case No. 4:18-CV-00500-JM; Apr. 21, 2020; pp. 1-56.

*Zest Labs, Inc. v Walmart*; ECF No. 274; Walmart; "Defendant's Reply Brief in Support of Its Motion To Exclude Proposed Expert Testimony of Mark Lanning"; United States District Court for the Eastern District of Arkansas; Case No. 4:18-CV-00500-JM; Apr. 21, 2020; pp. 1-22.

*Zest Labs, Inc. v Walmart*; ECF No. 275; Zest Labs, Inc. et al.; "Zest Labs Inc.'s Motion for Partial Summary Judgment That Walmart Used and Disclosed Zest's Information in the Walmart Applications"; United States District Court for the Eastern District of Arkansas; Case No. 4:18-CV-00500-JM; Apr. 21, 2020; pp. 1-4.

*Zest Labs, Inc. v Walmart*; ECF No. 276; Zest Labs, Inc. et al.; "Plaintiffs' Motion To Exclude Testimony of Walmart's Expert, Dr. David P. Dobkin"; United States District Court for the Eastern District of Arkansas; Case No. 4:18-CV-00500-JM; Apr. 21, 2020; pp. 1-3.

*Zest Labs, Inc. v Walmart*; ECF No. 277; Zest Labs, Inc. et al.; "Brief in Support of Plaintiffs' Motion To Exclude the Testimony of Walmart's Expert Witness, Dr. David P. Dobkin"; United States District Court for the Eastern District of Arkansas; Case No. 4:18-CV-00500-JM; Apr. 21, 2020; pp. 1-59.

*Zest Labs, Inc. v Walmart*; ECF No. 278; Zest Labs, Inc. et al.; "Plaintiffs' Motion To Exclude Testimony of Walmart Expert, Dr. Catherine Adams Hutt"; United States District Court for the Eastern District of Arkansas; Case No. 4:18-CV-00500-JM; Apr. 21, 2020; pp. 1-4.

*Zest Labs, Inc. v Walmart*; ECF No. 279; Zest Labs, Inc. et al.; "Brief in Support of Plaintiffs' Motion To Exclude the Testimony of Walmart's Expert Witness, Dr. Catherine Adams Hutt"; United States District Court for the Eastern District of Arkansas; Case No. 4:18-CV-00500-JM; Apr. 21, 2020; pp. 1-64.

*Zest Labs, Inc. v Walmart*; ECF No. 280; Zest Labs, Inc. et al.; "Zest Labs Inc.'s Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-4.

*Zest Labs, Inc. v Walmart*; ECF No. 281; Zest Labs, Inc. et al.; "Plaintiffs' Motion To Exclude Testimony of Walmart's Damages Expert, Dr. William Choi"; United States District Court for the Eastern District of Arkansas; Case No. 4:18-CV-00500-JM; Apr. 21, 2020; pp. 1-4.

*Zest Labs, Inc. v Walmart*; ECF No. 282; Zest Labs, Inc. et al.; "Plaintiffs' Brief in Support of Motion To Exclude Testimony of Walmart's Damages Expert, Dr. William Choi"; United States District Court for the Eastern District of Arkansas; Case No. 4:18-CV-00500-JM; Apr. 21, 2020; pp. 1-30.

*Zest Labs, Inc. v Walmart*; ECF No. 283; Zest Labs, Inc. et al.; "Zest Labs Inc.'s Brief in Support of Its Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-159.

*Zest Labs, Inc. v Walmart*; ECF No. 284; Zest Labs, Inc. et al.; "Zest Labs Inc.'s Brief in Support of Its Motion for Partial Summary Judgment That Walmart Used and Disclosed Zest Labs' Information in the Walmart Applications"; United States District Court for the Eastern District of Arkansas; Case No. 4:18-CV-00500-JM; Apr. 21, 2020; pp. 1-165.

*Zest Labs, Inc. v Walmart*; ECF No. 285; Zest Labs, Inc. et al.; "Zest Labs Inc.'s Motion for Summary Judgment On Its Claim for Breach of Contract"; United States District Court for the Eastern District of Arkansas; Case No. 4:18-CV-00500-JM; Apr. 21, 2020; pp. 1-3.

*Zest Labs, Inc. v Walmart*; ECF No. 286; Zest Labs, Inc. et al.; "Zest Labs Inc.'s Brief in Support of Its Motion for Summary Judgment On Its Claim for Breach of Contract"; United States District Court for the Eastern District of Arkansas; Case No. 4:18-CV-00500-JM; Apr. 21, 2020; pp. 1-30.

*Zest Labs, Inc. v Walmart*; ECF No. 287; Zest Labs, Inc. et al.; "Plaintiffs' Response To Defendant's Motion for Summary Judgment"; United States District Court for the Eastern District of Arkansas; Case No. 4:18-CV-00500-JM; Apr. 21, 2020; pp. 1-138.

*Zest Labs, Inc. v Walmart*; ECF No. 288; Zest Labs, Inc. et al.; "Plaintiffs' Opposition To Defendant's Motion To Exclude Testimony of Damages Expert Stephen L. Becker, Ph.D."; United States District Court for the Eastern District of Arkansas; Case No. 4:18-CV-00500-JM; Apr. 21, 2020; pp. 1-63.

*Zest Labs, Inc. v Walmart*; ECF No. 289; Zest Labs, Inc. et al.; "Plaintiffs' Brief in Opposition of Defendant's Motion To Exclude Proposed Expert Testimony of Patent Attorney Q. Todd Dickinson"; United States District Court for the Eastern District of Arkansas; Case No. 4:18-CV-00500-JM; Apr. 21, 2020; pp. 1-180.

*Zest Labs, Inc. v Walmart*; ECF No. 290; Zest Labs, Inc. et al.; "Plaintiffs' Brief in Opposition of Defendant's Motion To Exclude Proposed Expert Testimony of Mark Lanning"; United States District Court for the Eastern District of Arkansas; Case No. 4:18-CV-00500-JM; Apr. 21, 2020; pp. 1-62.

*Zest Labs, Inc. v Walmart*; ECF No. 291; Zest Labs, Inc. et al.; "Zest Labs Inc.'s Reply Brief in Support of Its Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-18.

*Zest Labs, Inc. v Walmart*; ECF No. 292; Zest Labs, Inc. et al.; "Plaintiffs' Reply in Support of Their Motion To Exclude Testimony of Walmart's Damages Expert Dr. William Choi"; United States District Court for the Eastern District of Arkansas; Case No. 4:18-CV-00500-JM; Apr. 21, 2020; pp. 1-20.

*Zest Labs, Inc. v Walmart*; ECF No. 293; Zest Labs, Inc. et al.; "Brief in Support of Plaintiffs' Motion To Exclude the Testimony of Walmart's Expert Witness, Dr. David P. Dobkin"; United States District Court for the Eastern District of Arkansas; Case No. 4:18-CV-00500-JM; Apr. 21, 2020; pp. 1-13.

*Zest Labs, Inc. v Walmart*; ECF No. 294; Zest Labs, Inc. et al.; "Zest Labs Inc.'s Reply in Support of Their Motion for Partial Summary Judgment That Walmart Used and Disclosed Zest's Information in the Walmart Application"; United States District Court for the Eastern District of Arkansas; Case No. 4:18-CV-00500-JM; Apr. 21, 2020; pp. 1-39.

*Zest Labs, Inc. v Walmart*; ECF No. 295; Zest Labs, Inc. et al.; "Plaintiffs' Reply in Support of Their Motion To Exclude the Testimony of Walmart's Expert Witness, Dr. Catherine Adams Hutt"; United States District Court for the Eastern District of Arkansas; Case No. 4:18-CV-00500-JM; Apr. 21, 2020; pp. 1-23.

(56) References Cited

OTHER PUBLICATIONS

*Zest Labs, Inc.* v *Walmart*; ECF No. 296; Zest Labs, Inc. et al.; "Plaintiffs' Objections To and Motion To Strike Evidence Cited in Walmart's Responses To Zest Labs, Inc.'s Statement of Material Facts in Support of Its Motions for Partial for Summary Judgement and Motion for Summary Judgment"; United States District Court for the Eastern District of Arkansas; Case No. 4:18-CV-00500-JM; Apr. 21, 2020; pp. 1-5.

*Zest Labs, Inc.* v *Walmart*; ECF No. 297; Zest Labs, Inc. et al.; "Plaintiffs' Memorandum in Support of Objections To and Motion To Strike Evidence Cited in Walmart's Responses To Zest Labs, Inc.'s Statement of Material Facts in Support of Its Motions for Partial for Summary Judgement and Motion for Summary Judgment"; United States District Court for the Eastern District of Arkansas; Case No. 4:18-CV-00500-JM; Apr. 21, 2020; pp. 1-5.

*Zest Labs, Inc.* v *Walmart*; ECF No. 298; Walmart; "Defendant's Consolidated Brief in Opposition To Plaintiffs' Objections To and Motions To Strike Evidence Cited By Walmart in Connection With Summary Judgment Motions"; United States District Court for the Eastern District of Arkansas; Case No. 4:18-CV-00500-JM; May 4, 2020; pp. 1-18.

USPTO; U.S. Appl. No. 15/653,786; Notice of Allowance and Fees Due (PTOL-85) dated Nov. 24, 2021; (pp. 1-6).

ReFED; "Retail Food Waste Action Guide"; https://www.refed.com/downloads/Retail_Guide_Web.pdf; 2018; pp. 1-44.

Zest Labs; "On-demand meal quality visibility from the restaurant to consumer delivery"; https://www.zestlabs.com/zest-delivery/; Available as early as Oct. 22, 2017; pp. 1-7.

Andrew Wilson, "Vision Software Blends into Food Processing", Jun. 1, 2012, pp. 1-13.

Cognex, "Introduction to Machine vision, A guide to automating process & quality improvements", pp. 1-24.

International Search Report and Written Opinion dated Nov. 4, 2019 in corresponding International Application No. PCT/US2019/043461.

S. Mandal et al., "Optimal production inventory policy for defective items with fuzzy lime period", Science Direct, Applied Mathematical modelling, vol. 34, Issue 3, Mar. 2010, pp. 1-27.

S. Ren, K. He, R. Girshick, and J. Sun. Faster R-CNN: Towards real-time object detection with region proposal networks. In NIPS, 2015. (Year: 2015).

USPTO; U.S. Appl. No. 16/521,741; Office Action dated Feb. 25, 2021.

USPTO; U.S. Appl. No. 16/521,741; Office Action dated Jun. 3, 2021.

USPTO; U.S. Appl. No. 16/521,741; Office Action dated Nov. 3, 2020.

USPTO; U.S. Appl. No. 16/596,966; Non-Final Rejection dated Feb. 23, 2022; (pp. 1-10).

\* cited by examiner

SYSTEM AND METHOD FOR THE DETERMINATION OF PRODUCE SHELF LIFE

RELATED APPLICATIONS

This application claims priority to Indian Patent Application No. 201811009903 entitled "SYSTEM AND METHOD FOR THE DETERMINATION OF PRODUCE SHELF LIFE," filed on Mar. 19, 2018, the content of which is hereby incorporated by reference in its entirety.

BACKGROUND

Supply chain systems monitor the movement of produce from an originating location through distribution channels to retail establishments.

BRIEF DESCRIPTION OF DRAWINGS

Illustrative embodiments are shown by way of example in the accompanying drawings and should not be considered as a limitation of the present disclosure.

DETAILED DESCRIPTION

Figure 1:
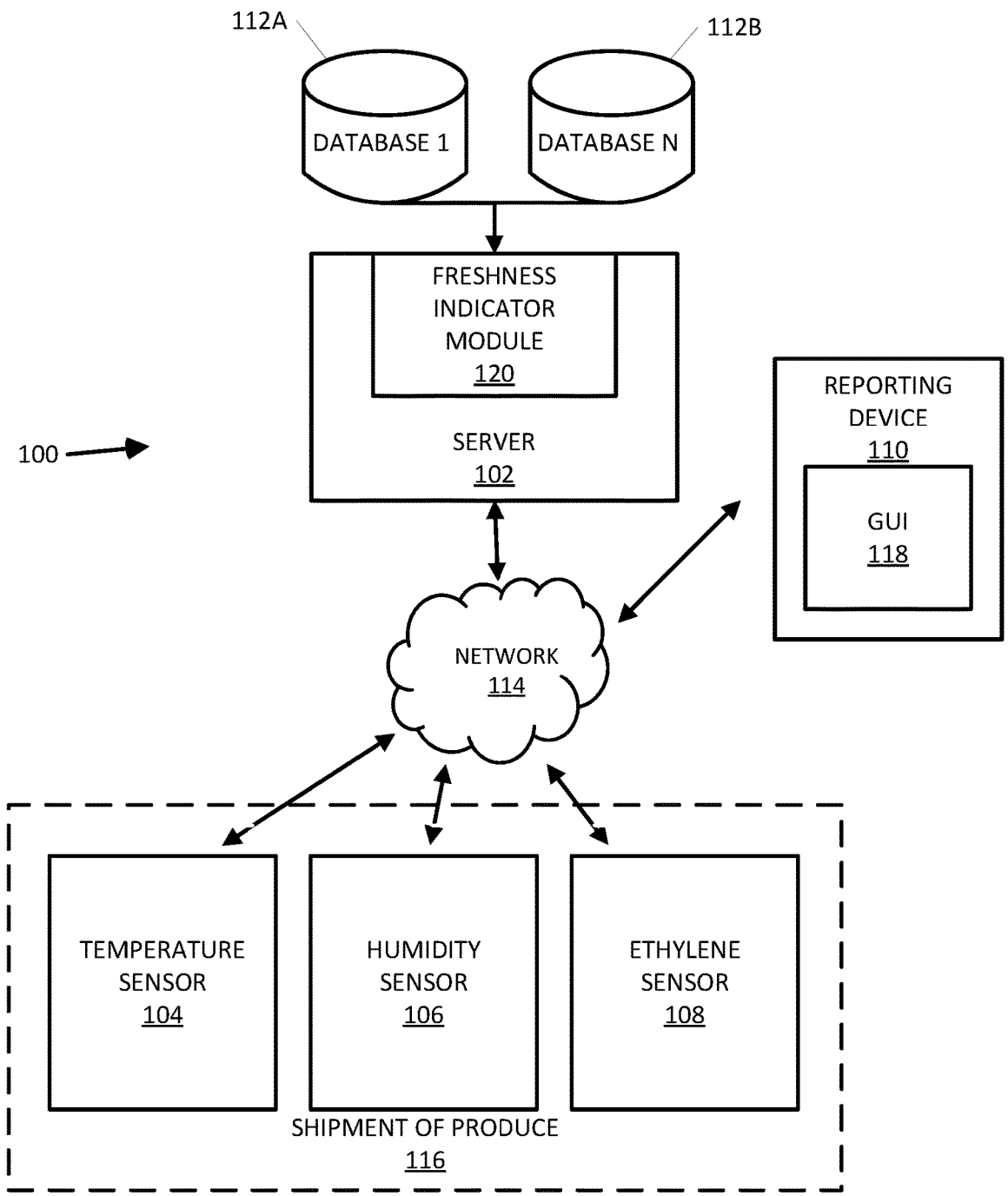
FIG. 1 is a block diagram illustrating a system for the determination of product shelf life in a supply chain environment according to an exemplary embodiment.

Described in detail herein is a system and method that receive periodic readings from sensors distributed throughout the produce supply chain that detect ambient characteristics including temperature, humidity, and ethylene exposure. The system utilizes the sensor readings in conjunction with time exposure readings to determine a sensitivity of each type of produce to each of the characteristics. The sensitivity value may be applied along with subsequent readings to determine the remaining shelf life of a product within the supply chain. Shipments in the supply chain can be rerouted or accelerated based on remaining shelf life determination.

In another embodiment, the system receives periodic readings from sensors distributed on unmanned aerial vehicles. The periodic reading determines exposure to temperature, humidity and ethylene during portions of the produce's travel through the supply chain. For example, the unmanned aerial vehicles may take temperature, humidity and ethylene readings at a farm from which the produce originates its trip through the supply chain.

In one embodiment, periodic readings may be taken of the produce at various points in time during the produce's travel through the supply chain. The images may include images recorded from imaging sensors to determine physical characteristics of the produce at different points within the supply chain.

A number of terms used to explain embodiments of the present invention are now discussed. For example, as used herein "shelf life" is the length of time that a commodity may be stored without becoming unfit for use, consumption, or sale. In other words, shelf life might refer to whether a commodity should no longer be on a pantry shelf (unfit for use), or just no longer on a supermarket shelf (unfit for sale, but not yet unfit for use). For produce commodities, the shelf life may be the time a product may be stored without becoming unsuitable for use or consumption.

"Remaining shelf life" is a key performance indicator (KPI) that may predict the remaining life of a produce item at every node in a supply chain "Dynamic expiration" date may be the estimated expiration date that is calculated using the estimated remaining life of the item. Like the KPI, the dynamic expiration also changes with the change in ambient conditions. Elements in the supply chain that impact the shelf life of a perishable item include: time, temperature, humidity, damage, ethylene content, packaging, and other treatments/processing.

"Temperature sensitivities" of an item may be a measure of how susceptible a produce item is to a change in temperature. The sensitivity of an item is the measure of the reduction of life (in hours) of an item when there is unit degree change in temperature for an hour. Similarly, there are sensitivities related to humidity, ethylene content, packaging standards and treatment based sensitivities. Sensitivities may be computed by retaining samples of items from a load at the distribution center. The samples may require to be kept at different ambient conditions and may require to be monitored every day until expiration. The collected shelf life may then be regressed against the temperature to derive the sensitivities.

FIG. 1 is a block diagram illustrating a system for the determination of product shelf life in a supply chain environment according to an exemplary embodiment. The system 100 includes a shipment of product 116, a plurality of sensors distributed throughout the product supply chain including a temperature sensor 104, a humidity sensor 106, and an ethylene sensor 108. The sensors are connected through a network 114 to a server 102. Communicatively coupled, either locally or remotely, are one or more databases 112A, 112B for storing produce shelf life information. A reporting device 110 with a corresponding graphical user interface (GUI) 118 may be used to inform a user of the state of produce shelf life within the supply chain. The server 102 hosts the execution of the freshness indicator module 120 which determines the remaining shelf life of a shipment of produce and updates the GUI 118.

As described in this non-limiting embodiment, a shipment of produce 116 may be monitored by one or more sensors. As illustrated in FIG. 1, the shipment of produce 116 may be monitored by a temperature sensor 104, a humidity sensor 106, and an ethylene sensor 108. In other embodiments, a shipment of produce 116 may include a combination and varying numbers of sensors placed at varying proximities to the shipment of produce 116. In another embodiment, a combination of sensors may be integrated into a facility where the shipment of produce 116 is transiting. In another embodiment, a combination of sensors may be integrated into the transportation vehicle moving the shipment of produce 116 or a facility at which the produce is stored. In another embodiment, a combination of sensors may be integrated into the packaging, such as a pallet, of the produce during transport.

The sensors may take the form of embedded computing devices. An embodiment of the embedded computing device may be an Internet of Things (IoT) device. Advantages of IoT devices include the utilization of well known operational software packages, low power consumption, and a small footprint. Additionally IoT software stacks provide support for many alternative communication implementations. As discussed above in one embodiment, sensors are physical integrated into the containers that the produce transits the supply chain inside. In another embodiment, sensors may be more remote to the produce (e.g. integrated into the hold of a truck) but proximate enough to measure temperature, humidity and ethylene. Likewise IoT devices may be distributed throughout a distribution facility to provide the periodic readings necessary to determine remaining shelf life.

The sensors may communicate over a network 114. Utilizing an IoT software stack as described above, the plurality of sensors may utilize lower level network transport including but not limited to NB-IoT or LTE-Cat M1. Additionally non-IoT focused transport can be utilized for the connectivity of the sensors including WiFi, Bluetooth, and cellular LTE networks. The network 114 may include WANs, LANs, and the Internet. In the supply chain, the network 114 may include public or private portions of the internet, including utilizing virtualized private network (VPN) connections for data security.

The sensors provide periodic readings of data over the network 114 to a server 102. The server 102 receives periodic readings from the data across all sensors within the system. In one embodiment, the server 102 may be a dedicated physical computing device, or alternatively the server 102 may be a virtualized software server environment executing across a multiple computing devices.

Databases 112A, 112B catalog and index received periodic readings from the sensors. The databases 112A, 112B may be locally attached storage or area attached storage. The databases 112A, 112B may contain historical information utilized to identify characteristics of produce shipments indicative of various levels of remaining shelf life. The databases 112A, 112B may contain additional historical information utilized to train a machine learning algorithm, including a support vector machine, to characterize readings from the sensors as indicative of various states of remaining shelf life.

A reporting device 110 may be attached directly to the server 102, or more commonly, the reporting device 110 is communicatively attached through the network 114 to the server 102. In some embodiments, the reporting device 110 may be a mobile device such as a mobile phone or tablet. The reporting device 110 may include a display capable of rendering the graphical user interface (GUI) 118.

The GUI 118 may receive indications of remaining shelf life and display the remainders in an easy to read format. In some embodiments, the GUI 118 can display details regarding a shipment of produce and indicate a remaining time period corresponding to the remaining shelf life of the items in the shipment. It should be appreciated that a shipment may include one type of produce or multiple types of produce and each may have separate remaining shelf lives. Alternatively, the GUI 118 may provide a user with an indication to hold a shipment of produce based on the remaining shelf life. Holding a shipment of produce at a location may allow a user prevent a shipment of produce from proceeding to a location that may adversely affect the remaining shelf life so that the produce is unmarketable. The GUI 118 may provide a user an indication to reroute a shipment of produce based on the remaining shelf life. Based on current sensor readings at the current location of the shipment of produce, GUI 118 can display an indication that a shipment of produce is in jeopardy of exhausting its remaining shelf life, and prompt the user to relocate the shipment of produce where it can be sold while still viable.

Server 102 executes freshness indicator module 120. The freshness indicator module 120 evaluates the periodic readings from the sensors. The freshness indicator module 120 may require specific data to calculate the shelf life remaining. For example, in one embodiment, in a supply chain, the freshness indicator module 120 may require measurements for: supplier pick ambient temperatures (temperature at time of picking of the produce), supplier pack ambient temperature (temperature at time of packing of the produce), trailer ambient temperatures (temperature at time of shipping of the produce), distribution center ambient temperatures (temperature at time of intermediate storing of the produce) and a store ambient temperature (temperature at time of selling of the produce). Likewise for humidity, the freshness indicator module 120 may require: supplier pick ambient humidity, supplier pack ambient humidity, trailer ambient humidity, distribution center ambient humidity, and store ambient humidity. Similarly for ethylene readings, the freshness indicator module 120 may require: supplier pick ethylene, supplier pack ethylene, trailer ethylene, distribution center ethylene, and store ethylene.

Time intervals for the various periods for which the readings may occur may be determined for a number of different time periods occurring at a number of different phases during the transit of the produce through the supply chain. For example, time intervals may determined with reference to: pick date time, pack date time, cool date time, supplier ship date time, distribution receive date time, distribution center ship date time, store receive data time, store shelf replenishment data time, and store point of sale date time. Based on the date times collected throughout the supply chain, corresponding time intervals may be determined by subtracting combinations of the recorded dates. For example: Pick to cool/pack is the difference of the cool date time less the pick date time. Likewise, readings within the same phase (e.g. while produce is being stored at a distribution center) may also be used to determine how long produce was exposed to a particular temperature (or other types of readings).

"Ambient variations" as described herein are the differences between the ambient temperatures recorded at every point within the supply chain and a predetermined optimal/acceptable standard for that type of produce and reading. For example an ambient temperature variation is the difference of the measured ambient temperature less the standard temperature for the type of produce. Likewise ambient humidity variation is the difference of the measured ambient humidity less the standard humidity for the type of produce. For ethylene sensitive items, the ambient ethylene volume less the standard ethylene volume.

For calculating sensitivity, in one embodiment, retention sampling and other experimentation may be performed to arrive at the temperature, humidity and ethylene sensitivities of an item. At the farm or the distribution center, samples from harvest or shipments may be retained in various temperature and humidity zones and time to decay may be monitored for all the samples in order to get the life duration. After the experimentation; a regression may be used to arrive at the sensitivities expressed at:

$$SL=(S_T*\text{Temp})+(S_H*\text{Humidity})+(S_E*\text{Ethylene})+\text{Error Value}$$

where, $S_T$ is the temperature sensitivity, $S_H$ is the humidity sensitivity, $S_E$ is the ethylene sensitivity, and SL is the shelf life of the items.

The remaining shelf life can be generated by the freshness indicator module at any point in the supply chain. In an embodiment, the freshness indicator module takes into account the time spent from harvest of the produce and the time/life lost (in hrs. or min.) due to changes in ambient temperature, humidity and ethylene content. The remaining shelf life may then be determined with the calculation expressed by:

Product Shelf Life−((Produce Age)+($\Sigma S_T$*Time of Temperature deviation*Temperature Deviation)+ ($\Sigma S_H$*Time of Humidity deviation*Humidity Deviation)+($\Sigma S_E$*Time of Ethylene deviation*Ethylene Deviation))

Upon the calculation of the remaining shelf life, the freshness indicator module 120 may update the GUI 118 over the network.

Figure 2:
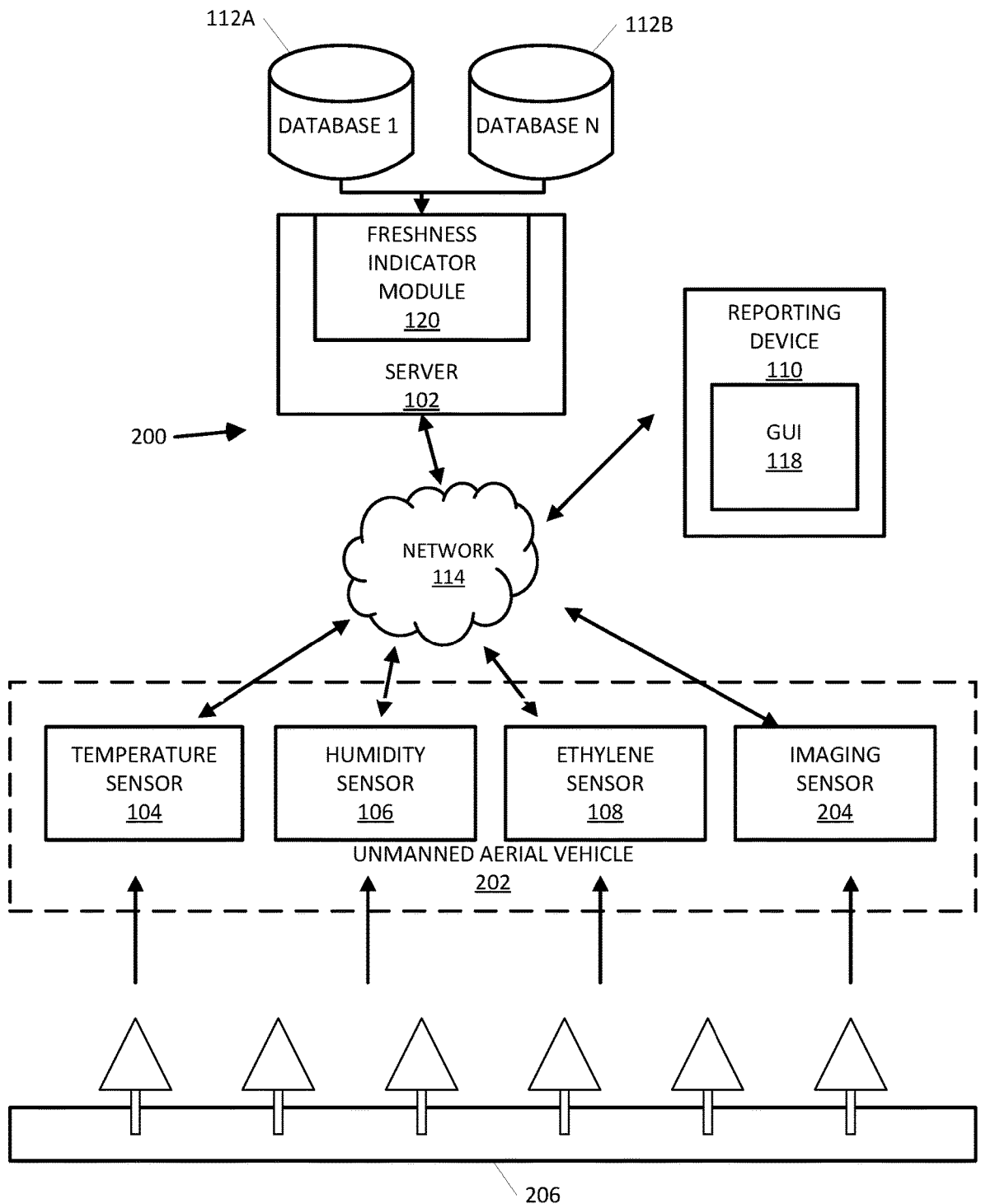
FIG. 2 is a block diagram illustrating a system for the determination of product shelf life in a supply chain environment utilizing an unmanned aerial vehicle according to an exemplary embodiment.

FIG. 2 is a block diagram illustrating a system 200 for the determination of product shelf life in a supply chain environment utilizing an unmanned aerial vehicle according to an exemplary embodiment. Similar to the system embodied in FIG. 1, the computational and reporting components (e.g. the server 102, the reporting device 110, and the network 114) maintain their described functionality. In FIG. 2, some of the sensors in the system are affixed to an unmanned aerial vehicle 202. Additionally, an imaging sensor 204 in the unmanned aerial vehicle 202 may augment the sensors array. In addition to the periodic readings taken corresponding to FIG. 1, the unmanned aerial vehicle 202 may include imaging of the origination of the supply chain. In one embodiment, the imaging may include that of supplier crops 206 in the field prior to and during harvest. Alternatively, the imaging may include harvested produce. This imaging may be supplemented with images not taken by the unmanned aerial vehicle 202, such as but not limited to images taken with a handheld imaging device, showing produce in cool rooms prior to shipping, produce in distribution centers and produce in store. The images may be transmitted back to the freshness indicator module 120. The freshness indicator module 120 may process the imaging by identifying a set of characteristics present in the imaging indicative of remaining shelf life. For example, color changes of produce may be a characteristic indicative of remaining shelf life. Other defects of produce, such as skin reflectivity, may be characteristics indicative of remaining shelf life. The freshness indicator module 120 compares the set of characteristics extracted from the imaging and compares them to a set of known control characteristics. The known control characteristics may be determined through experimentation and stored in the databases 112A, 112B (e.g. as a library of images). Based on the comparison, the freshness indicator module 120 may correlate a remaining shelf life of the produce from the control. Additionally, the characteristic comparison may be utilized in conjunction with the measurements and calculations as described regarding FIG. 1 to provide better accuracy in predicting remaining shelf life. The combination of both approaches may also provide training inputs for a machine learning algorithm for additional confidence.

Figure 3:
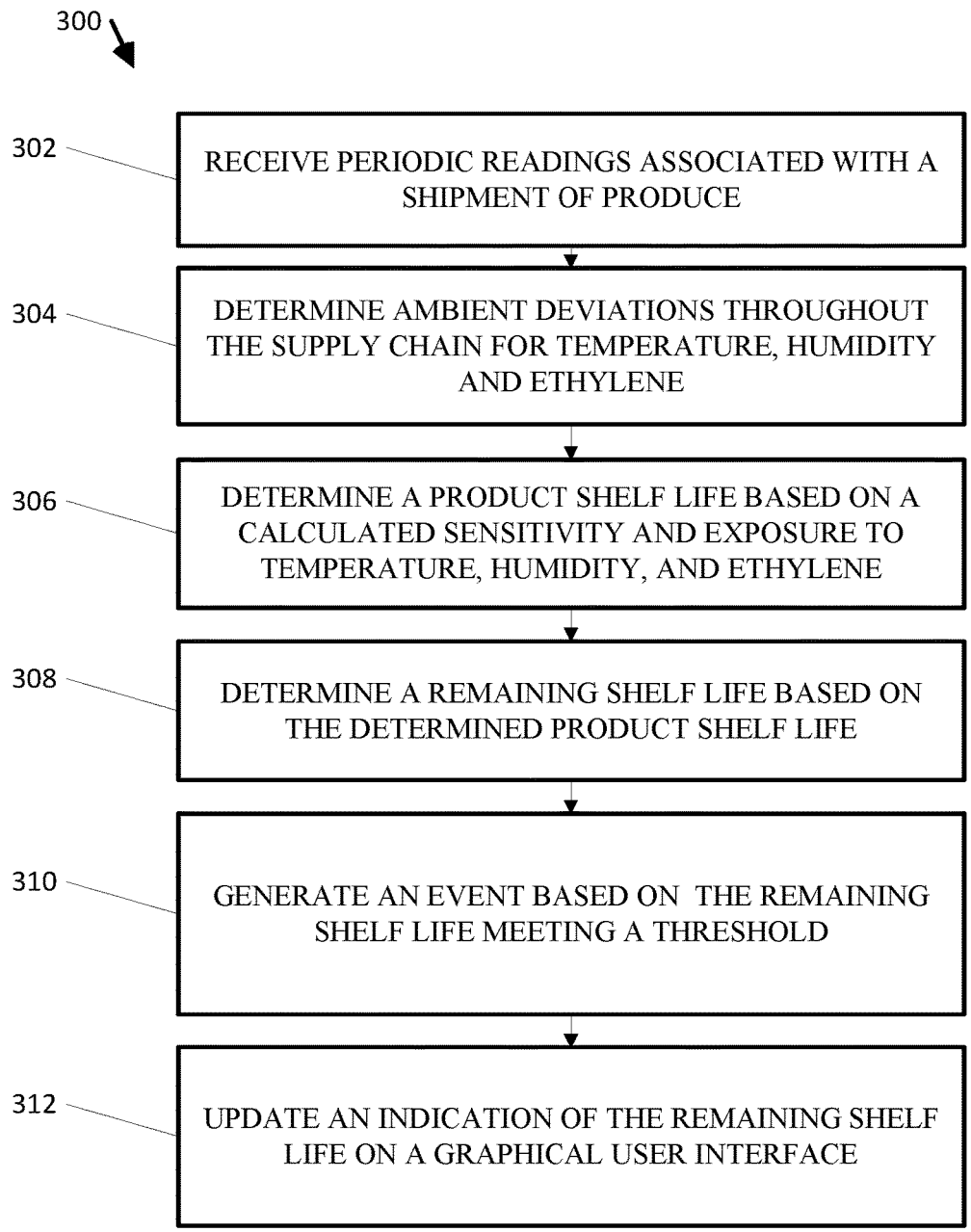
FIG. 3 is a flow diagram illustrating a system for the determination of product shelf life in a supply chain environment according to an exemplary embodiment.

FIG. 3 is a flow diagram illustrating a system for the determination of product shelf life in a supply chain environment according to an exemplary embodiment.

At step 302, the freshness indicator module receives periodic readings associated with a shipment of produce from sensors distributed at locations throughout a produce supply chain. The locations may include an initial location at which the produce originated. Additional locations may include the transportation vehicles, distribution centers, and stores.

At step 304, the freshness indicator module determines ambient deviations throughout the supply chain for temperature, humidity and ethylene. Pre-defined criteria for the shipment of produce may be based at least in part on the periodic readings and utilized to build confidence in the remaining shelf life determinations.

At step 306, the freshness indicator module determines a product shelf life based on a calculated sensitivity to temperature in conjunction with an amount of time of temperature deviation and an amount of temperature deviation, a calculated sensitivity to humidity in conjunction with an amount of time of humidity deviation and an amount of humidity deviation, and calculated sensitivity to ethylene in conjunction with an amount of time of ethylene deviation and an amount of ethylene deviation. The freshness indicator module may calculate a sensitivity to temperature, a sensitivity to humidity, and a sensitivity to ethylene for the shipment of produce based at least in part on the periodic readings.

The calculation of a sensitivity to temperature, a sensitivity to humidity, and a sensitivity to ethylene for the shipment of produce may be calculated using machine learning to periodically recalculate sensitivity based on additional readings received from the sensors. Training and periodic validation of the machine learning algorithm may be utilized to provide data points in a supervised learning activity.

At step 308, the freshness indicator module determines a remaining shelf life based on the determined product shelf life, an age of the shipment of produce, and conditions of the shipment of product in transit, the remaining shelf life representing a time period the shipment of produce is fit for sale.

At step 310, freshness indicator module generates an event based on the remaining shelf life meeting a threshold. A first threshold may correspond to the produce becoming unfit for sale. In one embodiment, the freshness indicator module may automatically divert the shipment of produce to another location based on the event. Alternatively, the freshness indicator module may automatically hold the shipment of product at one location based on the event. Additionally, the freshness indicator module may generate a second event based on the remaining life meeting a second threshold. The second threshold may indicate that the produce is unfit for consumption. The freshness indicator may update an indication on a graphical user interface corresponding to the second event, indicating the shipment of produce has no remaining shelf life and is unfit for consumption.

At step 312, the freshness indicator module updates an indication of the remaining shelf life on a graphical user interface. The update can include a number of actions a user may take based on the remaining shelf life. For example, if the remaining shelf life is no longer fit for sale, the user may be presented with an option to generate orders to discard the shipment.

Figure 4:
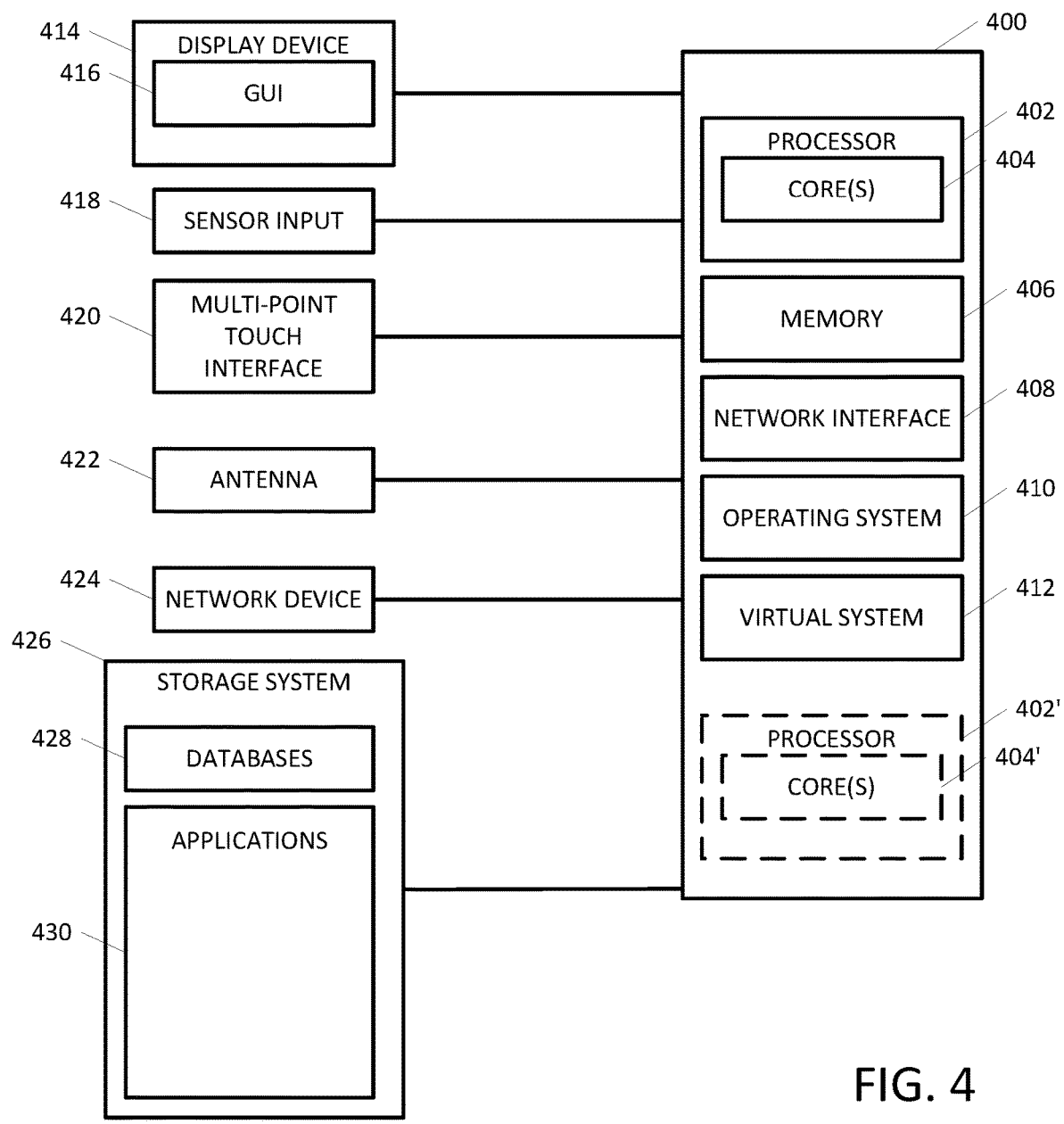
FIG. 4 depicts a block diagram of an exemplary computing device in accordance with an exemplary embodiment

FIG. 4 is a block diagram of an example computing device for implementing exemplary embodiments of the present disclosure. Embodiments of the computing device 400 can implement embodiments of the system for the determination of product shelf life in a supply chain environment. For example, the computing device can be embodied as a portion of the server 102, sensors 104, 106, 108, 204, and reporting devices 110. The computing device 400 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 406 included in the computing device 400 may store computer-readable and computer-executable instructions or software (e.g., the GUI 118) for implementing exemplary operations of the computing device 400. The computing device 400 also includes configurable and/or programmable processor 402 and associated core(s) 404, and optionally, one or more additional configurable and/or programmable processor(s) 402' and associated core(s) 404' (for example, in the case of computer systems having multiple processors/cores), for executing computer-readable and computer-executable instructions or software stored in the memory 406 and other programs for implementing exemplary embodiments of the present disclosure. Processor 402 and processor(s) 402' may each be a single core processor or multiple core (404 and 404') processor. Either or both of processor 402 and processor(s) 402' may be configured to execute one or more of the instructions described in connection with computing device 400.

Virtualization may be employed in the computing device 400 so that infrastructure and resources in the computing device 400 may be shared dynamically. A virtual machine 412 may be provided to handle a process running on multiple processors so that the process appears to be using only one computing resource rather than multiple computing resources. Multiple virtual machines may also be used with one processor.

Memory 406 may include a computer system memory or random access memory, such as DRAM, SRAM, EDO RAM, and the like. Memory 406 may include other types of memory as well, or combinations thereof. The computing device 400 can receive data from input/output devices. A user may interact with the computing device 400 through a visual display device 414, such as a computer monitor, which may display one or more graphical user interfaces 416, multi touch interface 420 and a sensor input 418 corresponding to the sensor 104, 106, 108, 204 being employed.

The computing device 400 may also include one or more storage devices 426, such as a hard-drive, CD-ROM, or other computer readable media, for storing data and computer-readable instructions and/or software that implement exemplary embodiments of the present disclosure (e.g., GUI 118). For example, exemplary storage device 426 can include one or more databases 428 for storing information associated sensor reading and data related to product shelf life. The databases 428 may be updated manually or automatically at any suitable time to add, delete, and/or update one or more data items in the databases.

The computing device 400 can include a network interface 408 configured to interface via one or more network devices 424 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing system can include one or more antennas 422 to facilitate wireless communication (e.g., via the network interface) between the computing device 400 and a network and/or between the computing device 400 and other computing devices. The network interface 408 may include a built-in network adapter, network interface card, PCMCIA network card, card bus network adapter, wireless network adapter, USB network adapter, modem or any other device suitable for interfacing the computing device 400 to any type of network capable of communication and performing the operations described herein.

The computing device 400 may run any operating system 410, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device 400 and performing the operations described herein. In exemplary embodiments, the operating system 410 may be run in native mode or emulated mode. In an exemplary embodiment, the operating system 410 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components or method steps, those elements, components, or steps can be replaced with a single element, component, or step. Likewise, a single element, component, or step can be replaced with multiple elements, components, or steps that serve the same purpose. Moreover, while exemplary embodiments have been shown and described with references to particular embodiments thereof, those of ordinary skill in the art will understand that various substitutions and alterations in form and detail can be made therein without departing from the scope of the present disclosure. Further, still, other aspects, functions, and advantages are also within the scope of the present disclosure.

Exemplary flowcharts are provided herein for illustrative purposes and are non-limiting examples of methods. One of ordinary skill in the art will recognize that exemplary methods can include more or fewer steps than those illustrated in the exemplary flowcharts and that the steps in the exemplary flowcharts can be performed in a different order than the order shown in the illustrative flowcharts.

We claim:

1. A system for determining a shelf life of produce within a supply chain comprising:
   a plurality of sensors distributed at a plurality of locations throughout a produce supply chain, the plurality of locations including an initial location at which the produce originated;
   an imaging sensor, wherein the imaging sensor is configured to capture images of the produce;
   a computing device communicatively coupled to the plurality of sensors and configured to execute a freshness indicator module, the freshness indicator module when executed:
      receiving periodic readings from the plurality of sensors associated with a shipment of produce,
      determining ambient deviations throughout the supply chain for temperature, humidity and ethylene from pre-defined criteria for the shipment of produce based at least in part on the periodic readings, calculating a sensitivity to temperature, a sensitivity to humidity, and a sensitivity to ethylene for the shipment of produce based at least in part on the periodic readings, wherein the calculation of the sensitivity to temperature, the sensitivity to humidity, and the sensitivity to ethylene for the shipment of produce is calculated using machine learning to periodically recalculate sensitivity based on additional readings received from the plurality of sensors, determining a product shelf life based on the calculated sensitivity to temperature in conjunction with an amount of time of temperature deviation and an amount of temperature deviation, the calculated sensitivity to humidity in conjunction with an amount of time of humidity deviation and an amount of humidity deviation, and the calculated sensitivity to ethylene in conjunction with an amount of time of ethylene deviation and an amount of ethylene deviation, capturing, via the imaging sensor, an image of the shipment of produce, determining a first set of characteristics within the image of the shipment of produce, comparing the first set of characteristics against a second set of characteristics consistent with a known condition of a control shipment of the produce, determining a remaining shelf life based on the determined product shelf life, an age of the shipment of produce, conditions of the shipment of product in transit, and the comparison of the first set of characteristics against the second set of characteristics, the remaining shelf life representing a time period the shipment of produce is fit for sale, generating an event based on the remaining shelf life meeting a threshold, and updating an indication of the remaining shelf life on a graphical user interface.

2. The system of claim 1, wherein the plurality of sensors include temperature sensors, humidity sensors, and ethylene sensors and are affixed to an unmanned aerial vehicle.

3. The system of claim 1, wherein the product shelf life is calculated using the equation:

$$SL=(S_T*\text{Temp})+(S_H*\text{Humidity})+(S_E*\text{Ethylene})+\text{Error Value}.$$

4. The system of claim 1, wherein the remaining life is calculated using the equation:

Product Shelf Life−((Produce Age)+($\Sigma S_T$*Time of Temperature deviation*Temperature Deviation)+($\Sigma S_H$*Time of Humidity deviation*Humidity Deviation)+($\Sigma S_E$*Time of Ethylene deviation*Ethylene Deviation)).

5. The system of claim 1, the freshness indicator module when executed further:

generates a second event based on the remaining life traversing a second threshold, and updates an indication on a graphical user interface corresponding to the second event, wherein the indication represents the remaining life corresponds to the shipment of produce being unfit for consumption.

6. A method for determining shelf life of produce within a supply chain comprising:

receiving periodic readings associated with a shipment of produce from a plurality of sensors distributed at a plurality of locations throughout a produce supply chain, the plurality of locations including an initial location at which the produce originated;

determining ambient deviations throughout the supply chain for temperature, humidity and ethylene from pre-defined criteria for the shipment of produce based at least in part on the periodic readings;

calculating a sensitivity to temperature, a sensitivity to humidity, and a sensitivity to ethylene for the shipment of produce based at least in part on the periodic readings, wherein the calculation of the sensitivity to temperature, the sensitivity to humidity, and the sensitivity to ethylene for the shipment of produce is calculated using machine learning to periodically recalculate sensitivity based on additional readings received from the plurality of sensors;

determining a product shelf life based on the calculated sensitivity to temperature in conjunction with an amount of time of temperature deviation and an amount of temperature deviation, the calculated sensitivity to humidity in conjunction with an amount of time of humidity deviation and an amount of humidity deviation, and the calculated sensitivity to ethylene in conjunction with an amount of time of ethylene deviation and an amount of ethylene deviation;

capturing, via an imaging sensor, an image of the shipment of produce;

determining a first set of characteristics within the image of the shipment of produce;

comparing the first set of characteristics against a second set of characteristics consistent with a known condition of a control shipment of the produce;

determining a remaining shelf life based on the determined product shelf life, an age of the shipment of produce, conditions of the shipment of product in transit, and the comparison of the first set of characteristics against the second set of characteristics, the remaining shelf life representing a time period the shipment of produce is fit for sale;

generating an event based on the remaining shelf life meeting a threshold; and updating an indication of the remaining shelf life on a graphical user interface.

7. The method of claim 6, further comprising:

diverting the shipment of produce to another location or holding the shipment of produce at one location based on the event.

8. The method of claim 6, wherein the product shelf life is calculated using the equation:

$$SL=(S_T*\text{Temp})+(S_H*\text{Humidity})+(S_E*\text{Ethylene})+\text{Error Value}.$$

9. The method of claim 6, wherein the remaining life is calculated using the equation:

Product Shelf Life−((Produce Age)+($\Sigma S_T$*Time of Temperature deviation*Temperature Deviation)+($\Sigma S_H$*Time of Humidity deviation*Humidity Deviation)+($\Sigma S_E$*Time of Ethylene deviation*Ethylene Deviation)).

10. The method of claim 6, further comprising:

generating a second event based on the remaining life traversing a second threshold, and updating an indication on a graphical user interface corresponding to the second event, wherein the indication represents the remaining life corresponds to the shipment of produce being unfit for consumption.

11. A non-transitory computer readable medium holding instructions for determining shelf life of produce within a supply chain, the instructions when executed by a processor causing at least one computing device to:

receive periodic readings associated with a shipment of produce from a plurality of sensors distributed at a plurality of locations throughout a produce supply chain, the plurality of locations including an initial location at which the produce originated;

determine ambient deviations throughout the supply chain for temperature, humidity and ethylene from pre-defined criteria for the shipment of produce based at least in part on the periodic readings;

calculate a sensitivity to temperature, a sensitivity to humidity, and a sensitivity to ethylene for the shipment of produce based at least in part on the periodic readings, wherein the calculation of the sensitivity to temperature, the sensitivity to humidity, and the sensitivity to ethylene for the shipment of produce is calculated using machine learning to periodically recalculate sensitivity based on additional readings received from the plurality of sensors;

determine a product shelf life based on the calculated sensitivity to temperature in conjunction with an amount of time of temperature deviation and an amount of temperature deviation, the calculated sensitivity to humidity in conjunction with an amount of time of humidity deviation and an amount of humidity deviation, and the calculated sensitivity to ethylene in conjunction with an amount of time of ethylene deviation and an amount of ethylene deviation, capture, via an imaging sensor, an image of the shipment of produce;

determine a first set of characteristics within the image of the shipment of produce;

compare the first set of characteristics against a second set of characteristics consistent with a known condition of a control shipment of the produce;

determine a remaining shelf life based on the determined product shelf life, an age of the shipment of produce, conditions of the shipment of product in transit, and the comparison of the first set of characteristics against the second set of characteristics, the remaining shelf life representing a time period the shipment of produce is fit for sale;

generate an event based on the remaining shelf life meeting a threshold; and update an indication of the remaining shelf life on a graphical user interface.

12. The medium of claim 11, wherein the product shelf life is calculated using the equation:

$$(S_T*\text{Temp})+(S_H*\text{Humidity})+(S_E*\text{Ethylene})+\text{Error}.$$

13. The medium of claim 11, wherein the remaining life is calculated using the equation:

$$\text{Product Shelf Life}-((\text{Produce Age})+(\Sigma S_T*\text{Time of Temperature deviation}*\text{Temperature Deviation})+(\Sigma S_H*\text{Time of Humidity deviation}*\text{Humidity Deviation})+(\Sigma S_E*\text{Time of Ethylene deviation}*\text{Ethylene Deviation})).$$

* * * * *